(12) United States Patent
Deininger et al.

(10) Patent No.: US 10,828,127 B2
(45) Date of Patent: Nov. 10, 2020

(54) MACHINING OF ENCLOSURES FOR IMPLANTABLE MEDICAL DEVICES

(71) Applicant: MEDTRONIC, INC., Minneapolis, MN (US)

(72) Inventors: Steven T. Deininger, Blaine, MN (US); Michael J. Baade, Zimmerman, MN (US); Charles E. Peters, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 15/650,665

(22) Filed: Jul. 14, 2017

(65) Prior Publication Data

US 2018/0015290 A1 Jan. 18, 2018

Related U.S. Application Data

(63) Continuation of application No. 13/449,428, filed on Apr. 18, 2012, now Pat. No. 10,286,218, which is a continuation-in-part of application No. 12/847,830, filed on Jul. 30, 2010, now abandoned, said application No. 13/449,428 is a continuation-in-part (Continued)

(51) Int. Cl.
*A61N 1/375* (2006.01)
*A61B 90/50* (2016.01)
*A61N 1/18* (2006.01)

(52) U.S. Cl.
CPC .............. *A61B 90/50* (2016.02); *A61N 1/18* (2013.01); *A61N 1/3752* (2013.01); *A61N 1/3754* (2013.01)

(58) Field of Classification Search
CPC .... A61N 1/375; A61N 1/3752; A61N 1/3968; A61N 1/37512; Y10S 439/909
See application file for complete search history.

(56) References Cited

U.S. PATENT DOCUMENTS 4,254,775 A * 3/1981 Langer ............................. 607/5
5,470,345 A * 11/1995 Hassler et al. .................. 607/36
(Continued)

OTHER PUBLICATIONS

U.S. Appl. No. 12/847,830—Appeal Decision dated Mar. 9, 2017.
(Continued)

*Primary Examiner* — Tammie K Marlen
(74) *Attorney, Agent, or Firm* — Withers & Keys, LLC

(57) ABSTRACT

Enclosures for implantable medical devices are machined from biocompatible materials using processes such as electric discharge machining and/or milling. Material is machined to create an enclosure. The enclosure may include an enclosure sleeve that has top and bottom caps added where the enclosure sleeve is machined either as a whole or as two separate halves that are subsequently joined together. During construction, circuitry is installed and where the enclosure includes an enclosure sleeve, the open top and bottom may be closed by caps while a connector block module may be mounted to the complete enclosure. The machining process allows materials that are typically difficult to stamp, such as grade 5 and 9 titanium and 811 titanium, that are beneficial to telemetry and recharging features of an implantable medical device to be used while allowing for an enclosure with a relatively detailed geometry and relatively tight tolerances.

20 Claims, 44 Drawing Sheets

Related U.S. Application Data of application No. PCT/US2012/022071, filed on Jan. 20, 2012, said application No. 13/449,428 is a continuation-in-part of application No. PCT/US2012/022086, filed on Jan. 20, 2012, said application No. 15/650,665 is a continuation of application No. 13/449,446, filed on Apr. 18, 2012, now Pat. No. 10,449,373, which is a continuation-in-part of application No. 12/847,830, filed on Jul. 30, 2010, now abandoned, and a continuation-in-part of application No. PCT/US2012/022086, filed on Jan. 20, 2012, and a continuation-in-part of application No. PCT/US2012/022071, filed on Jan. 20, 2012.

(60) Provisional application No. 61/230,549, filed on Jul. 31, 2009, provisional application No. 61/436,600, filed on Jan. 26, 2011.

(56) References Cited

U.S. PATENT DOCUMENTS

| | | | | |
|---|---|---|---|---|
| 6,083,640 | A * | 7/2000 | Lee et al. | 429/94 |
| 6,297,943 | B1 * | 10/2001 | Carson | 361/500 |
| 9,572,993 | B2 | 2/2017 | Deininger et al. | |
| 9,597,518 | B2 | 3/2017 | Deininger et al. | |
| 10,646,719 | B2 | 5/2020 | Deininger | |
| 2002/0165588 | A1 | 11/2002 | Fraley et al. | |
| 2006/0015150 | A1 * | 1/2006 | Rusin et al. | 607/36 |
| 2006/0161204 | A1 * | 7/2006 | Colvin | A61N 1/05 607/2 |
| 2006/0212087 | A1 * | 9/2006 | Haller | A61N 1/375 607/41 |
| 2007/0248881 | A1 * | 10/2007 | Scott et al. | 429/211 |
| 2008/0033500 | A1 * | 2/2008 | Strother et al. | 607/36 |

OTHER PUBLICATIONS

U.S. Appl. No. 13/449,446—Final Office Action dated Dec. 27, 2016.
U.S. Appl. No. 13/449,446—Response to Final Office Action dated Feb. 27, 2017.
U.S. Appl. No. 13/449,446—Advisory Action dated Mar. 6, 2017.
U.S. Appl. No. 13/449,446—Response dated Mar. 22, 2017.
U.S. Appl. No. 13/449,446—Response dated Sep. 14, 2017.
U.S. Appl. No. 13/449,446—Office Action dated Jun. 14, 2017.
U.S. Appl. No. 13/449,446—Final Office Action dated Sep. 29, 2017.
U.S. Appl. No. 13/449,446—After Final Response dated Nov. 29, 2017.
U.S. Appl. No. 13/449,446—Advisory Action dated Dec. 27, 2017.
U.S. Appl. No. 13/449,446—RCE Amendments dated Jan. 26, 2018.
U.S. Appl. No. 13/449,446—Office Action dated Mar. 21, 2018.
U.S. Appl. No. 13/449,428—Final Office Action dated Jan. 23, 2017.
U.S. Appl. No. 13/449,428—Response dated Mar. 23, 2017.
U.S. Appl. No. 13/449,428—Office Action dated May 22, 2017.
U.S. Appl. No. 13/449,428—Response dated Aug. 22, 2017.
U.S. Appl. No. 13/449,428—Final Office Action dated Sep. 20, 2017.
U.S. Appl. No. 13/449,428—Response dated Nov. 20, 2017.
U.S. Appl. No. 13/449,428—Advisory Action dated Dec. 13, 2017.
U.S. Appl. No. 13/449,428—Appeal Brief dated Mar. 22, 2018.
U.S. Appl. No. 15/464,328—Office Action dated Jan. 17, 2018.
U.S. Appl. No. 15/464,328—Response dated Apr. 17, 2018.

* cited by examiner

MACHINING OF ENCLOSURES FOR IMPLANTABLE MEDICAL DEVICES

RELATED APPLICATIONS

This present application claims priority to and is a continuation of U.S. patent application Ser. No. 13/449,428, filed Apr. 18, 2012, and entitled "CONNECTOR ENCLOSURE ASSEMBLIES OF MEDICAL DEVICES INCLUDING AN ANGLED LEAD PASSAGEWAY" which claims priority to and is a continuation-in-part of U.S. patent application Ser. No. 12/847,830, now abandoned, filed Jul. 30, 2010, and entitled "MACHINING OF ENCLOSURES FOR IMPLANTABLE MEDICAL DEVICES," which claims priority to U.S. Provisional Patent Application No. 61/230,549, filed Jul. 31, 2009, and entitled "MACHINING OF ENCLOSURES FOR IMPLANTABLE MEDICAL DEVICES." Both cases are incorporated by reference as if entirely rewritten herein. U.S. patent application Ser. No. 13/449,428 also claims priority to and is a continuation-in-part of International Application Serial No. PCT/US2012/022071, filed Jan. 20, 2012, and entitled "Implantable Medical Devices and Related Connector Enclosure Assemblies Utilizing Conductors Electrically Coupled to Feedthrough Pins"; and U.S. patent application Ser. No. 13/449,428 claims priority to and is a continuation-in-part of International Application Serial No. PCT/US2012/022086, filed Jan. 20, 2012, and entitled "Implantable Medical Devices and Related Connector Enclosure Assemblies Utilizing Conductors Electrically Coupled to Feedthrough Pins", both of which claim priority to U.S. Patent Application Ser. No. 61/436,600, filed Jan. 26, 2011, and entitled "Implantable Medical Devices and Related Connector Enclosure Assemblies Utilizing Conductors Electrically Coupled to Feedthrough Pins", each of which is incorporated by reference as if entirely rewritten herein.

This present application also claims priority to and is a continuation of U.S. patent application Ser. No. 13/449,446, filed Apr. 18, 2012, and entitled "CONNECTOR ENCLOSURE ASSEMBLIES OF MEDICAL DEVICES INCLUDING AN ANGLED LEAD PASSAGEWAY" which claims priority to and is a continuation-in-part of U.S. patent application Ser. No. 12/847,830, now abandoned, filed Jul. 30, 2010, and entitled "MACHINING OF ENCLOSURES FOR IMPLANTABLE MEDICAL DEVICES," which claims priority to U.S. Provisional Patent Application No. 61/230,549, filed Jul. 31, 2009, and entitled "MACHINING OF ENCLOSURES FOR IMPLANTABLE MEDICAL DEVICES." Both cases are incorporated by reference as if entirely rewritten herein. U.S. patent application Ser. No. 13/449,446 also claims priority to and is a continuation-in-part of International Application Serial No. PCT/US2012/022071, filed Jan. 20, 2012, and entitled "Implantable Medical Devices and Related Connector Enclosure Assemblies Utilizing Conductors Electrically Coupled to Feedthrough Pins"; and U.S. patent application Ser. No. 13/449,446 claims priority to and is a continuation-in-part of International Application Serial No. PCT/US2012/022086, filed Jan. 20, 2012, and entitled "Implantable Medical Devices and Related Connector Enclosure Assemblies Utilizing Conductors Electrically Coupled to Feedthrough Pins", both of which claim priority to U.S. Patent Application Ser. No. 61/436,600, filed Jan. 26, 2011, and entitled "Implantable Medical Devices and Related Connector Enclosure Assemblies Utilizing Conductors Electrically Coupled to Feedthrough Pins", each of which is incorporated by reference as if entirely rewritten herein.

TECHNICAL FIELD

Embodiments relate to enclosures for implantable medical devices. More particularly, embodiments relate to machining of the enclosures.

BACKGROUND

Implantable medical devices include an enclosure that houses the internal circuitry and other components that may be present. The enclosure may be constructed of a biocompatible material such as titanium which provides protection of the circuitry and other components. The enclosure may be hermetically sealed to prevent biological fluids from entering the enclosure and damaging the contents.

The enclosure is typically made of a material such as grade 1 titanium or other biocompatible materials of a similar hardness. Grade 1 titanium may be formed into the enclosure using stamping, where two enclosure halves are stamped from sheet stock material and are then welded together or otherwise attached to form the enclosure. While this grade 1 titanium enclosure provides adequate protection, the enclosure is less than ideal for implantable medical devices with features such wireless recharging and telemetry.

To accommodate these features, other grades of titanium have been used, such as grade 5 and grade 9 titanium as well as 811 titanium. These other grades of titanium typically cause less attenuation of recharging energy being directed into the enclosure and telemetry energy being directed into and out of the enclosure. However, grade 5 and 9 titanium as well as 811 titanium have a hardness or other characteristic that presents problems for the stamping process being used to form the two halves. This material may exhibit springback upon being formed which may cause the halves to exceed allowable dimension tolerances. Furthermore, the geometry that is available is restricted because relatively small radii, intricate details, and deep draws are difficult to achieve.

SUMMARY

Embodiments address issues such as these and others by providing for machining of enclosures using processes such as electric discharge machining and/or milling. Material is machined to create an enclosure, such as by machining an enclosure sleeve as a whole or by machining halves that may be attached at the sides. For the enclosure sleeve, circuitry is installed and the open top and bottom may be closed by caps while a connector block module may be mounted to the complete enclosure. The machining may be performed on various biocompatible materials including various grades of titanium including grade 5 and grade 9 titanium and 811 titanium.

DETAILED DESCRIPTION

Enclosures of implantable medical devices described herein may be created in various ways, such as by machining. Machining of the enclosures may also be done in various ways. For instance, machining may involve one or more forms of electric discharge machining (EDM), with wire EDM being particularly well suited to the machining of an enclosure sleeve as discussed below. Milling is another example of machining that may be done, alone or in combination with one or more forms of EDM. Other examples of machining are also applicable such as water jetting.

Figure 1A:
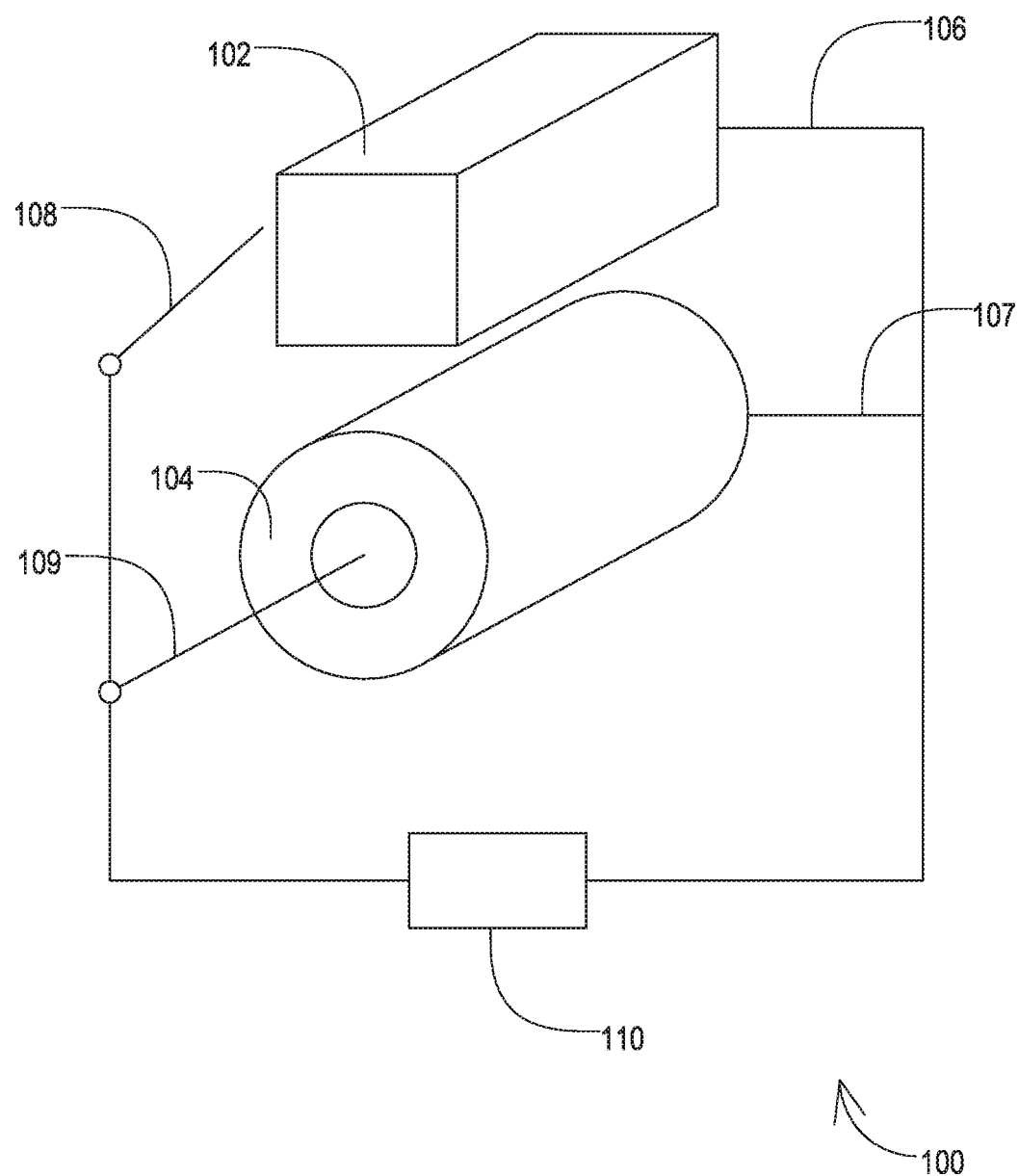
FIG. 1A shows an electric discharge process for machining at least a portion of an enclosure for an implantable medical device.

FIG. 1A shows an example of an electric discharge machining EDM process 100 that may be used according to various embodiments. This particular example employs wire EDM which may provide the ability to produce relatively tight radii and relatively detailed geometries, while wall thickness may be maintained at a uniform thickness or may be varied by design. The nature of the wire EDM process 100 dictates that an enclosure sleeve, or halves of an enclosure sleeve, be produced where the top and bottom are open. As discussed below, caps can then be attached to the enclosure sleeve to seal the top and bottom openings of the enclosure sleeve.

In this wire EDM example of machining, the initial workpiece may be of various forms. Two examples of workpieces are shown, a piece of bar stock material 102 and a piece of tubular stock material 104. The wire EDM process 100 may begin with either type of workpiece as well as others. The tubular workpiece 104 is particularly well suited to a wire EDM process where the enclosure is being machined as a whole. Considering the tubular workpiece 104 already has a hollow center where a wire 109 of the wire EDM process may be positioned, the inside geometry of the enclosure can be machined using the wire 109. For a bar workpiece 102, if the enclosure is to be wire EDM machined as a whole, then a hole must first be created within the bar workpiece 102 to allow placement of a wire 108 of the wire EDM so that the inside geometry can be machined using the wire 108.

The wire EDM process 100 uses an electrical power source 110 which applies a voltage potential between the wire 108/109 and an electrical contact 106/107 to the workpiece 102/104. The workpiece 102/104 is present within a dielectric bath. The repeated discharge from the wire 108/109 to the workpiece 102/104 repeatedly removes matter from the workpiece 102/104 to essentially provide a cutting effect. This cutting effect works even in the harder materials such as grade 5 titanium as well as in grade 9 titanium and 811 titanium and does not work harden the material such that an additional annealing step is not needed afterwards when wire EDM is used for the entire enclosure. The wire EDM process 100 may employ a variety of machining wires, including those having a diameter on the order of one ten-thousandth of an inch. Furthermore, a variety of power settings and speeds may be utilized for the wire EDM process 100, with slower speeds generally resulting in smoother surface finishes.

In some embodiments, the wire EDM process 100 may be used to machine the entire enclosure sleeve. In other embodiments, the wire EDM process 100 may be used for only a portion of the enclosure sleeve geometry, such as only the inside geometry, while another machining process such as another form of EDM or milling is used to create the outside or other remaining geometry.

Figure 1B:
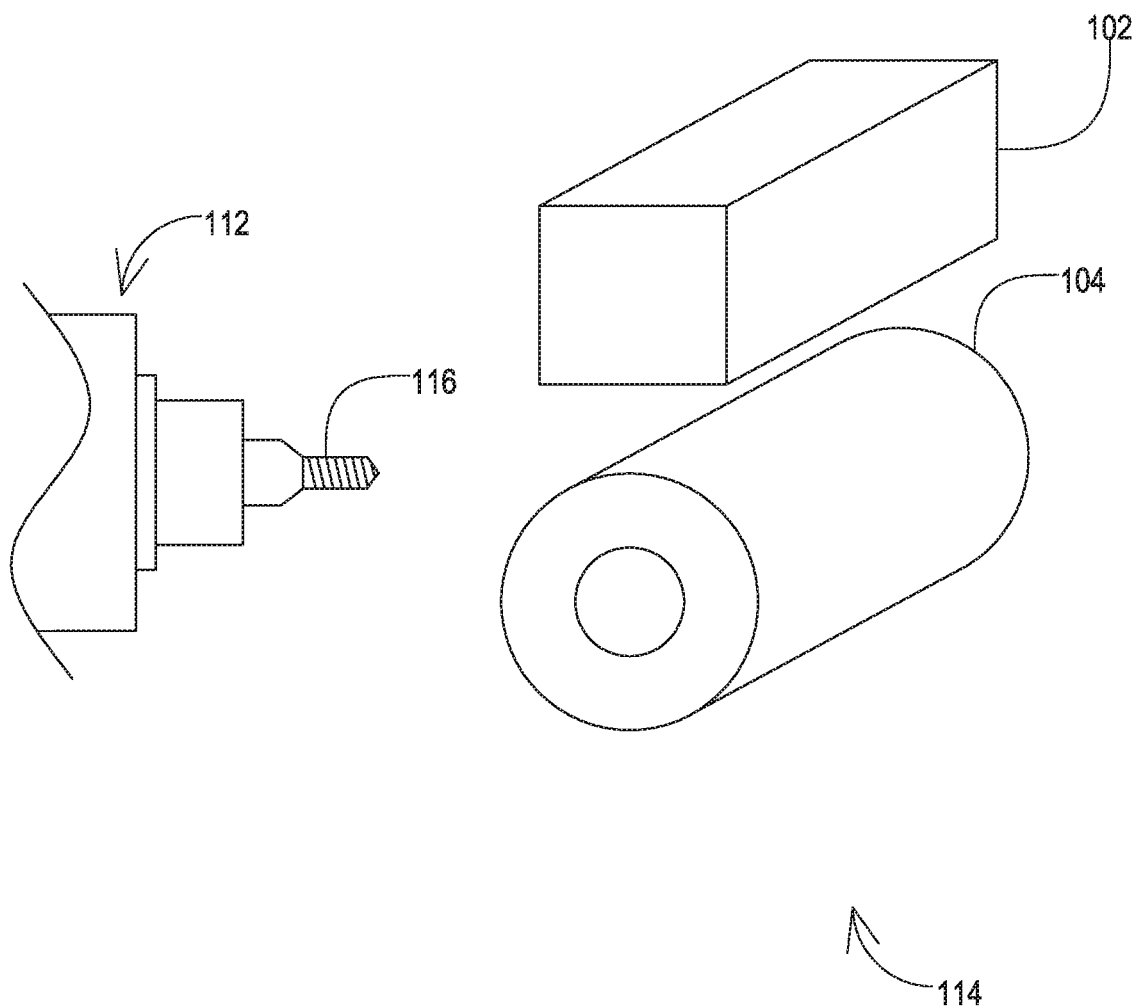
FIG. 1B shows a milling process for machining at least a portion of an enclosure for an implantable medical device.

FIG. 1B shows the milling process 114. Here a milling machine 112 includes a milling tool 116. This milling tool 116 is spun at a high angular velocity and brought into contact with the workpiece 102/104 to machine it to the appropriate geometry. One consequence of using milling for at least a portion of the enclosure geometry is that the workpiece 102/104 is work hardened. To account for this, the workpiece 102/104 once milled can be annealed.

In some embodiments, the milling process 114 may be used to machine the entire enclosure, whether in the form of a whole sleeve, enclosure sleeve halves with top and bottom caps, or as non-sleeve enclosure halves of conventional shape. In other embodiments, the milling process 114 may be used for only a portion of the enclosure sleeve geometry, such as only the outside geometry, while another machining process such as wire EDM is used to create the inside or other remaining geometry.

Figure 2:
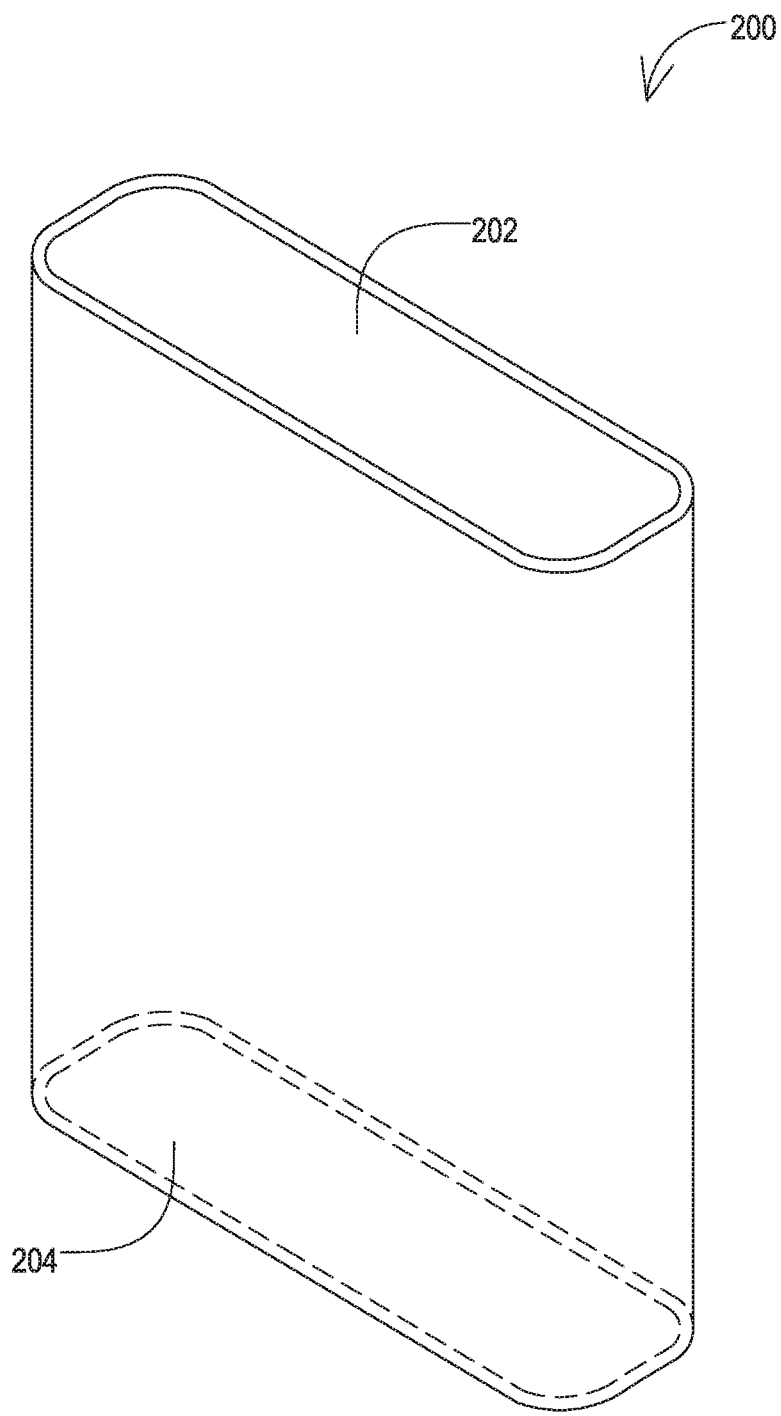
FIG. 2 shows an example of a machined enclosure for an implantable medical device.

FIG. 2 shows an example of a resulting enclosure sleeve 200 that has been machined as a whole according to various embodiments. The enclosure sleeve 200 includes an open top 202 and bottom 204 which may be capped during subsequent manufacturing steps once circuitry, desiccant, and the like are placed into the enclosure sleeve 200.

Figure 4A:
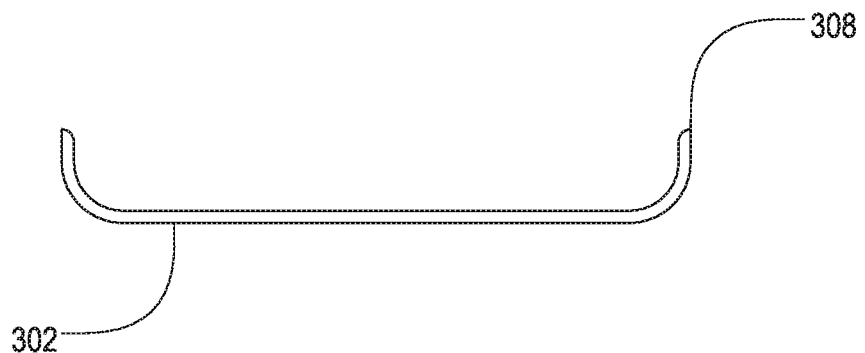
FIG. 4A is a top view of the machined enclosure half of FIG. 3A.

The enclosure sleeve 200 is shown with a particular symmetrical racetrack cross-section that is consistent from top to bottom. It will be appreciated that other cross-sections are applicable as well and that variations in the cross-section from top to bottom are also applicable. For instance, the wall thickness may vary at certain locations by design, which is a direct benefit of machining versus stamping. The wall thickness of the enclosure sleeve 200 may be machined to relatively thin amounts, such as 0.008 inch having a tolerance of 0.001 inch. Machining allows for other small details, such as a radiused edge 308, as shown in FIG. 4A, with a radius on the order of 0.008 inch.

Figures 3A, 3B:
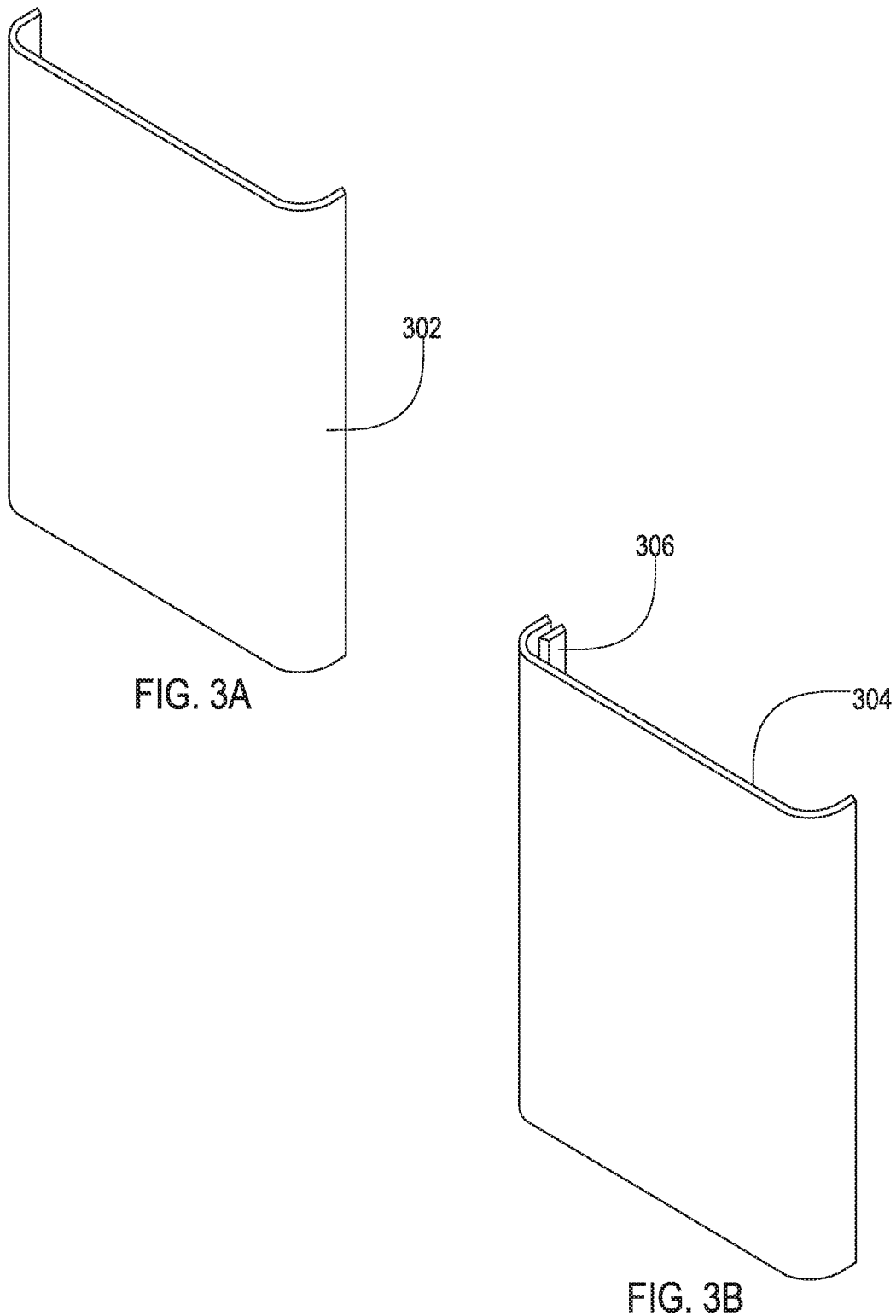
FIG. 3A is a perspective view of a machined enclosure half.
FIG. 3B is a perspective view of a machined enclosure half that attaches to the machined enclosure half of FIG. 3A to form an enclosure sleeve.

In some embodiments, the enclosure sleeve may not be machined as a whole but is instead machined as two separate halves that are subsequently brought together to form an enclosure sleeve similar to the enclosure sleeve 200 of FIG. 2. FIG. 3A shows an example of one enclosure sleeve half 302. FIG. 4A shows a top view of the enclosure sleeve half 302. In this example, the cross-section is consistent from top to bottom, but it will be appreciated that enclosure sleeve halves may be machined with variations in the cross-section from top to bottom including variation in wall thickness as well as variation in the cross-sectional shape.

Figure 4B:
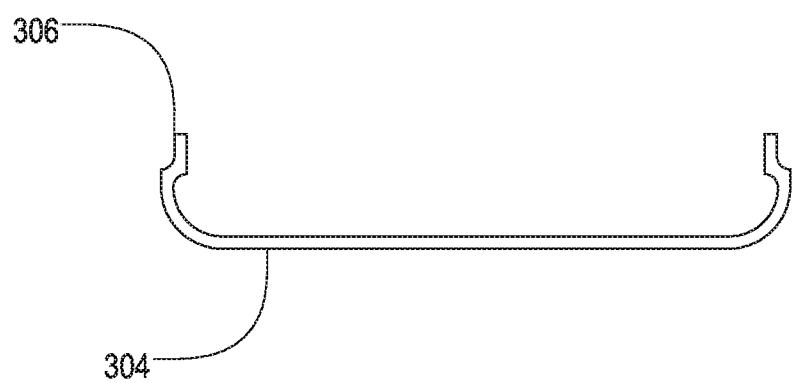
FIG. 4B is a top cross-sectional view of the machined enclosure half of FIG. 3B.
Figure 5A:
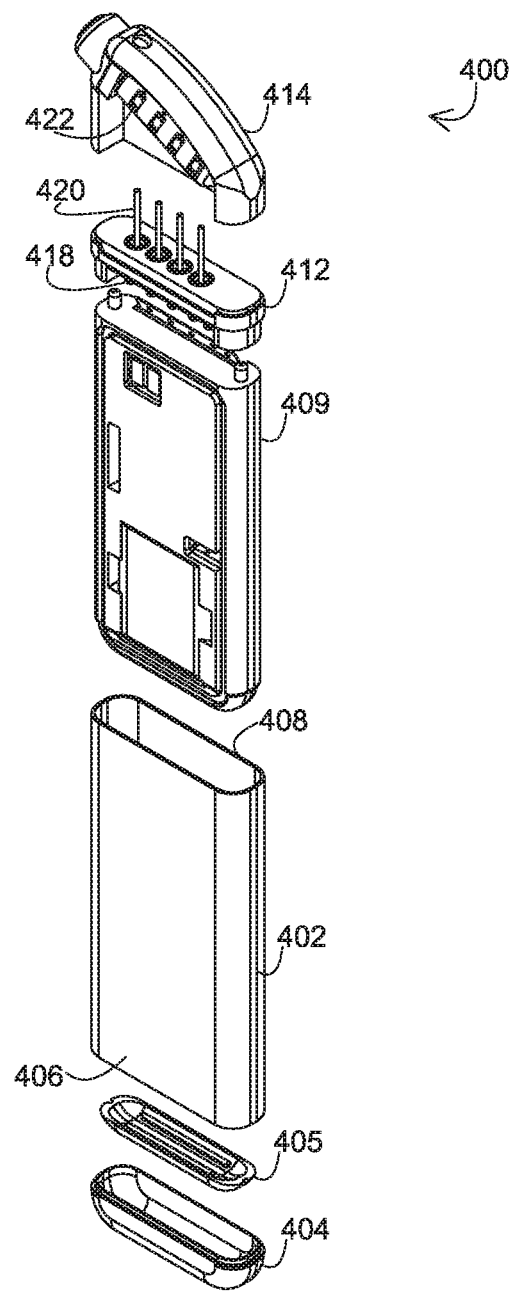
FIGS. 5A, 5B, 5C, and 5D are exploded perspective views of an illustrative embodiment of an implantable medical device having a connector enclosure assembly with an angled lead passageway according to various embodiments.
Figure 5B:
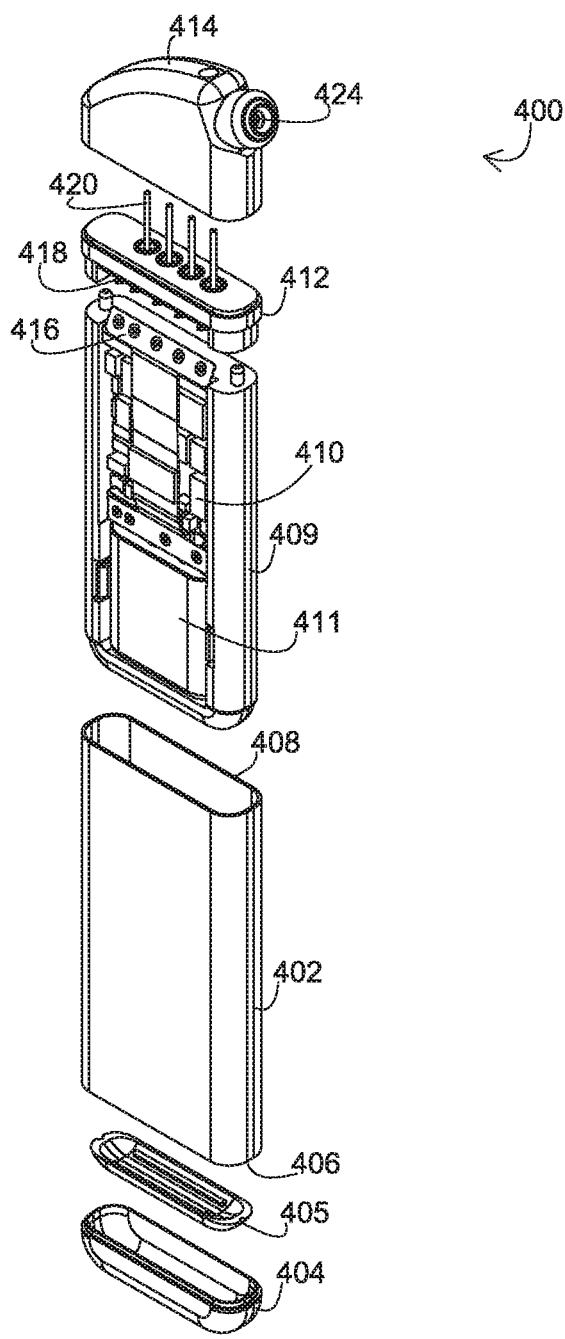
Figure 5C:
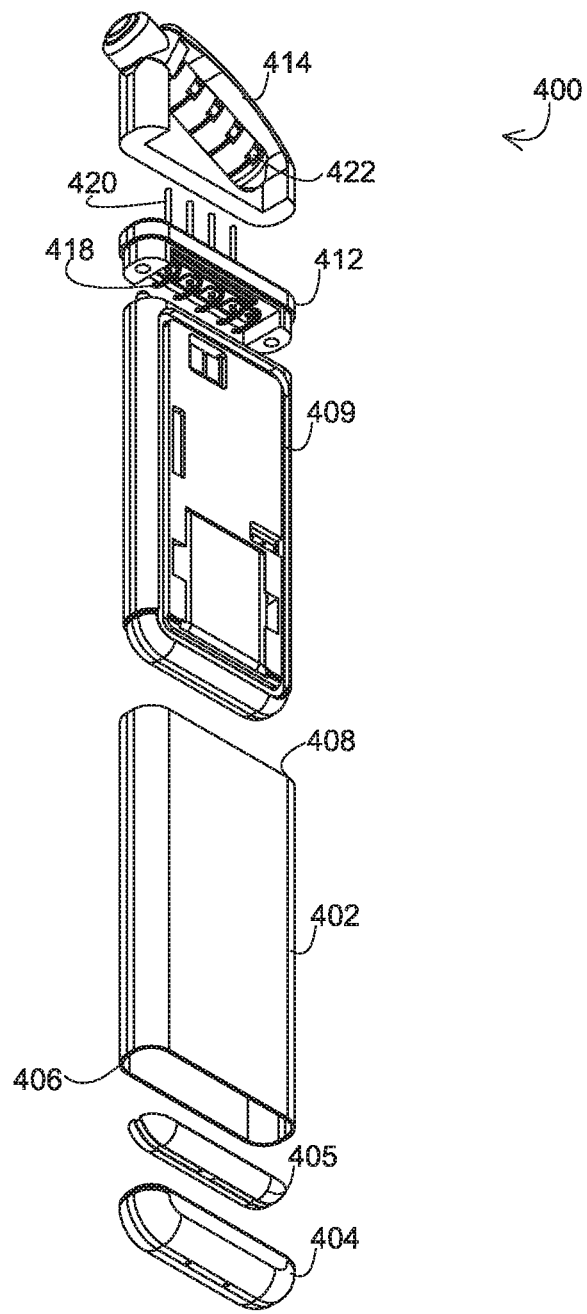
Figure 5D:
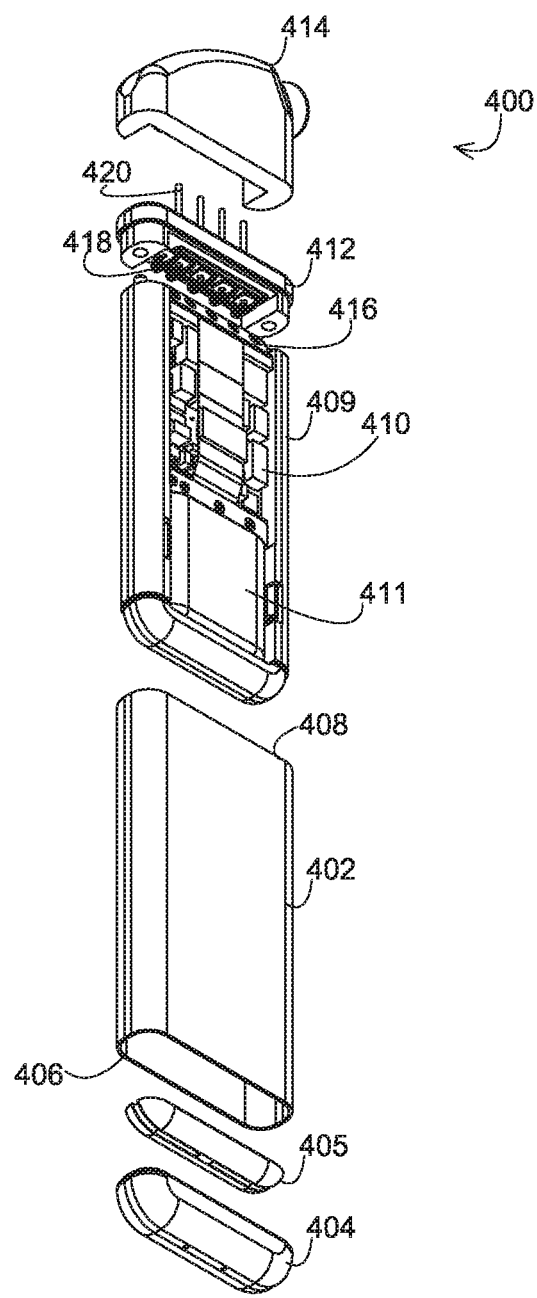

FIG. 3B shows an example of another enclosure sleeve half 304, and FIG. 4B shows the enclosure sleeve half 304 in cross-section. This enclosure sleeve half 304 is a mate to the enclosure sleeve half 302 of FIGS. 3A and 4A. A tab 306 is present on each vertical edge as oriented in the example of FIG. 3B. This tab 306 provides a supporting surface for the abutment of the inner side of the vertical edge of the enclosure sleeve half 302 to the vertical edge of the enclosure sleeve half 304. Thus, when laser seam welding is applied to the interfacing edges of the two halves 302, 304 to fix the two halves together to form the complete enclosure sleeve, the tab 306 supports that interface of the two edges during the weld and thereafter. This tab 306 also prevents the laser beam and melted titanium from entering the interior of the sleeve being formed by the two halves 302, 304. The tab 306 may include a radiused junction so as to be a closely matched negative of the radiused edge 308 of the enclosure sleeve half 302.

The tab 306 of this embodiment is shown as ending prior to reaching the top edge of the half 302. This allows space for a top cap discussed below to be seated into the top of the enclosure sleeve above the tab 306. However, in other embodiments the tab 306 may extend to the top edge of the half 302. In that case a top cap may have a notch that accepts the tab 306 as the top cap is being seated into the top of the enclosure sleeve.

FIGS. 5A-5D show exploded perspective views of an implantable medical device 400 that includes a machined enclosure. A machined enclosure sleeve 402 receives one or more circuit boards 410 that may include features such as a pulse generator for therapy stimulation, sensing circuitry for measuring physiological parameters, telemetry for communication with external devices, a power source, and a recharge circuit. The circuit board 410 of this example includes a flex circuit 416 that extends from the circuit board and carries stimulation and/or sensing signals between the circuitry and a feedthrough block 418 of a top cap 412 which passes the signals via pins 420 to a connector block module 414 which as shown is a partial construction of an example of a connector enclosure assembly. The circuit board 410 and an associated battery 411 reside within a polymer chassis 409 in this particular example. The chassis 409 fits snugly within the sleeve 402.

The top cap 412 is attached such as by a laser seam weld to a top edge 408 of the enclosure sleeve 402 to provide a sealed edge. The top cap 412 may be constructed of the same or different material than the enclosure sleeve 402. In this example, the top cap 412 includes the feedthrough block 418 from which the connector pins 420 extend to reach the lead connections 422 of the connector block module 414. For the top cap 412 as shown in FIGS. 5A-5D, this geometry may be machined using a milling process or other applicable machining techniques.

The connector block module 414 mounts to the top of the top cap 412. The top cap 412 may include barbs, pins, or other fasteners that engage receiving features on the bottom of the connector block module 414 to properly position and fix the connector block module 414 in place. The connector block module 414 may include ports that receive the connector pins 420 of the feedthrough block 418 and channel them to connectors 422 that are positioned within channel(s) 424. The channel(s) 424 receive leads that have connectors that mate to the connectors 422 and establish electrical continuity with the connector pins of the feedthrough block 418. One side of the connector block module 414 is shown transparently in FIGS. 5A, 5C, and 5D for purposes of illustrating the channel(s) 424 and connectors 422.

The connector block module 414 may be of a conventional polymer construction. However, the milling process allows the sleeve 402 to be significantly narrower than conventional IMD casings such that the connector block module 414 may also be significantly narrower. To the extent the connector block module 414 may be made so narrow that using conventional attachment features to the top cap 412 become unfeasible, the connector block module 414 may be encased by a metal, such as titanium, and that connector block encasement may be welded to the top cap 412 to provide a hermetic seal.

A bottom cap 404 is attached such as by a laser seam weld to a bottom edge 406 of the enclosure sleeve 402 to provide a sealed edge. As with the top cap 412, the bottom cap 404 may also be made of the same or different material than the enclosure sleeve 402, and may also be made of the same or different material than the top cap 412. The bottom cap 404 as shown has a bowl or canoe shape. This shape allows a desiccant 405 to be included in the bottom cap 404 and reside beneath the chassis 409 once the IMD 400 is assembled. For the bottom cap 404 as shown in FIGS. 5A-5D, this geometry may be machined using a milling process or other applicable machining techniques.

The desiccant 405 may also serve as a bumper between the chassis 409 and the bottom cap 404 for embodiments where the chassis 409 slides into position within the enclosure sleeve 402 and is held in place at least partially by contact with the bottom cap 404. However, in other embodiments, the desiccant 405 may be positioned elsewhere, such as in a pocket within the chasses 409 and in that case a separate bumper may be placed within the bottom cap 404. In other embodiments, where the chassis 409 is installed within a connector sleeve half so that sliding the chassis 409 within a complete connector sleeve 402 is not performed, the chassis 409 may be glued to the connector sleeve half to hold the chassis 409 in place and a bumper may be omitted particularly where the desiccant 405 is positioned within the chassis 409.

Figure 6:
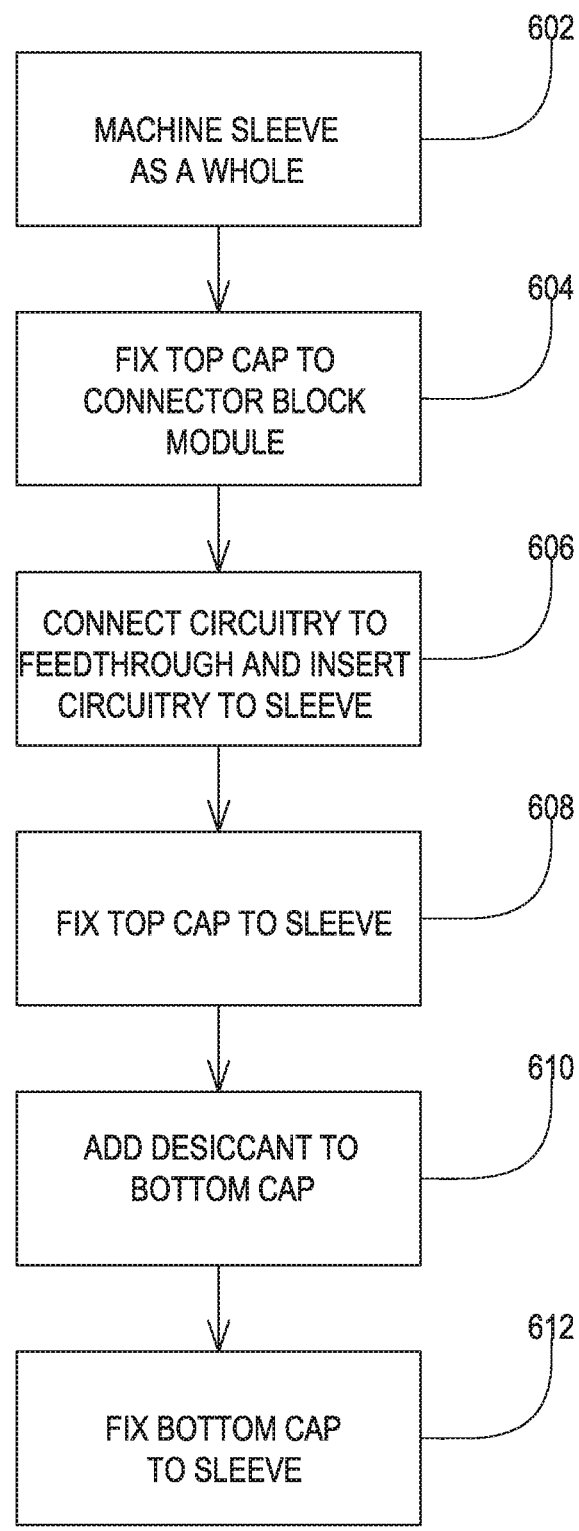
FIG. 6 shows one example of a set of manufacturing operations to produce an implantable medical device.

FIG. 6 shows one example of a manufacturing process for an implantable medical device with a machined enclosure. The process begins by machining an enclosure sleeve as a whole, such as that shown in FIG. 2, at a machining step 602. The enclosure sleeve may be machined as a whole by using any of the workpieces and machining processes previously discussed.

The top cap may be fixed to the connector block module by welding or other suitable means of attachment dependent upon the manner of construction of the connector block module as discussed above at a welding step 604. The electrical pins of the feedthrough block of the top cap are routed into the connector block module to make electrical contact with electrical connectors of the connector block module.

Once the top cap and connector block module are joined, the circuitry is connected to the feedthrough of the top cap and the circuitry is loaded into the sleeve at an insertion step 606. At this point, the top cap may then be attached to the sleeve, at an attachment step 608. The top cap may be laser seam or otherwise welded at the top edge of the sleeve.

At this point, a desiccant may be placed into the resting place formed in the bottom cap at a desiccant step 610. By completing the top construction before adding the desiccant and bottom cap, the addition of the desiccant can be delayed until the only remaining step is to add the bottom cap. In this manner, the desiccant is exposed to the ambient conditions for only a short time prior to the interior of the enclosure sleeve being isolated from the exterior. This preserves the effectiveness of the desiccant.

The bottom cap including the desiccant is then fixed to the enclosure sleeve via a laser seam or other weld at a welding step 612. At this point, the enclosure sleeve is sealed and the desiccant is exposed to only the moisture that is already within the enclosure sleeve.

Figure 7:
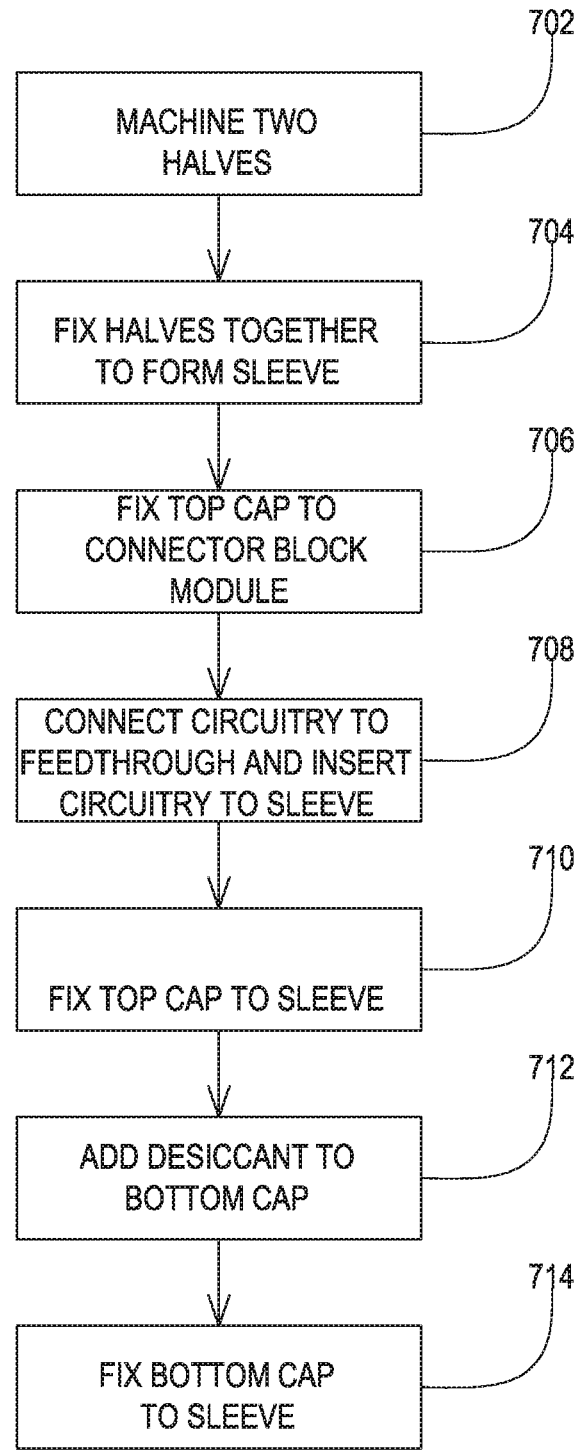
FIG. 7 shows another example of a set of manufacturing operations to produce an implantable medical device.

FIG. 7 shows another example of a manufacturing process for an implantable medical device with a machined enclosure. The process begins by machining an enclosure sleeve as two separate halves, such as those shown in FIGS. 3A and 3B, at a machining step 702. The enclosure sleeve halves may be machined using any of the workpieces and machining processes previously discussed.

Once the two complementary enclosure sleeve halves are complete, the two halves may be fixed together to form the enclosure sleeve at a welding step 704.

The top cap may be fixed to the connector block module at a connection step 706, where this connection may involve barbs, adhesives, and other conventional forms of connecting the connector block module or where the connector block module is encased in a metal such as titanium, the connection may be a weld. Once the top cap is joined to the connector block module, the circuitry is connected to the feedthrough of the top cap and the circuitry is loaded into the sleeve at an insertion step 708. The top cap may be attached to the enclosure sleeve at a welding step 710.

At this point, a desiccant may be placed into the bottom cap at a desiccant step 712. As with the process of FIG. 6, by completing the top construction before adding the bottom cap, the addition of the desiccant can be delayed until the only remaining step is to add the bottom cap. In this manner, the desiccant is exposed to the ambient conditions for only a short time prior to the interior of the enclosure sleeve being isolated from the exterior. This preserves the effectiveness of the desiccant.

The bottom cap is then fixed to the enclosure sleeve at a welding step 714. At this point, the enclosure sleeve is sealed and the desiccant is exposed to only the moisture that is already within the enclosure sleeve.

Figure 8:
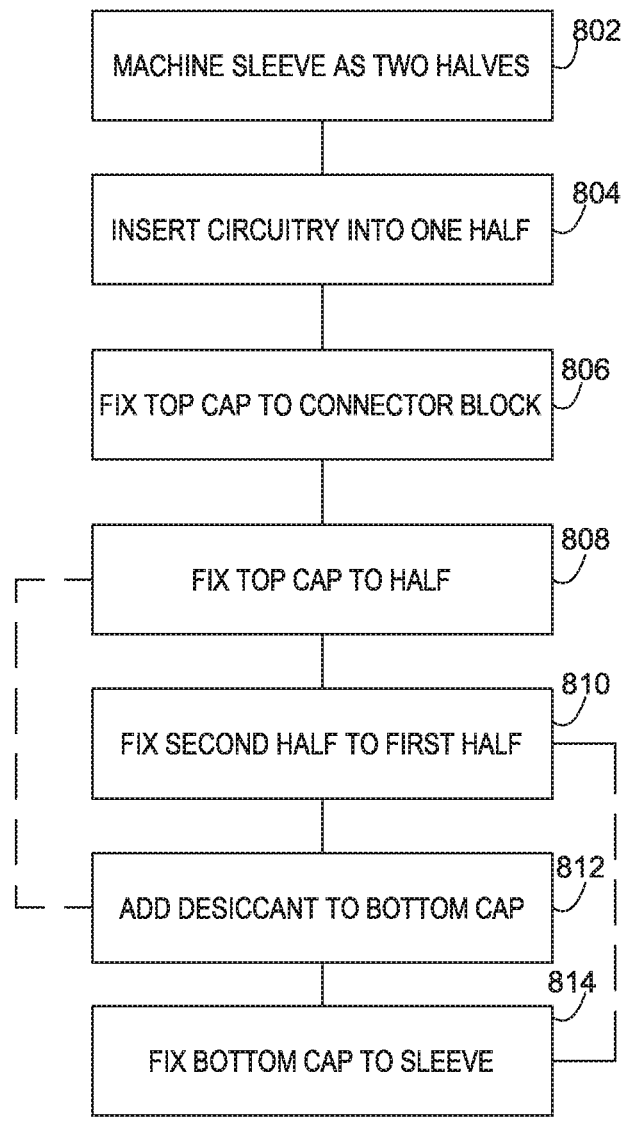
FIG. 8 shows another example of a set of manufacturing operations to produce an implantable medical device.

FIG. 8 shows another example of a manufacturing process for an implantable medical device with a machined enclosure. The process begins by machining an enclosure sleeve as two separate halves, such as those shown in FIGS. 3A and 3B, at a machining step 802. The enclosure sleeve halves may be machined using any of the workpieces and machining processes previously discussed.

Once at least one of the two complementary enclosure sleeve halves is complete, the circuitry may be placed into one of the halves at an insertion step 804. In conjunction with inserting the circuitry, the top cap may be fixed to the connector block module at a connection step 806, where this connection may involve barbs, adhesives, and other conventional forms of connecting the connector block module or where the connector block module is encased in a metal such as titanium, the connection may be a weld. Once the top cap is joined to the connector block module, the top cap may be attached to the enclosure sleeve half, with the electrical connections to the circuitry being completed, at an attachment step 808.

At this point, FIG. 8 presents alternative paths. In one example, the second half of the enclosure sleeve may be fixed to the first half to complete the sleeve at a welding step 810. A desiccant may then be placed into the bottom cap at a desiccant step 812, and the bottom cap is then fixed to the enclosure sleeve at a welding step 814. In another example, after attaching the top cap to the first half, the desiccant may then be placed into the bottom cap at a desiccant step 812, and the bottom cap is then fixed to the enclosure sleeve at a welding step 814. The second half of the enclosure sleeve is then attached to the first half at the welding step 810.

While the preceding examples of manufacturing involve the creation of an enclosure sleeve, other examples of manufacturing an implantable medical device with a machined enclosure are also applicable. For instance, rather than creating an enclosure sleeve as a whole or as two joined halves with top and bottom caps, two conventional halves may be milled rather than stamped. Circuitry, a connector block module, and desiccant may then be added in the conventional way.

Figure 9:
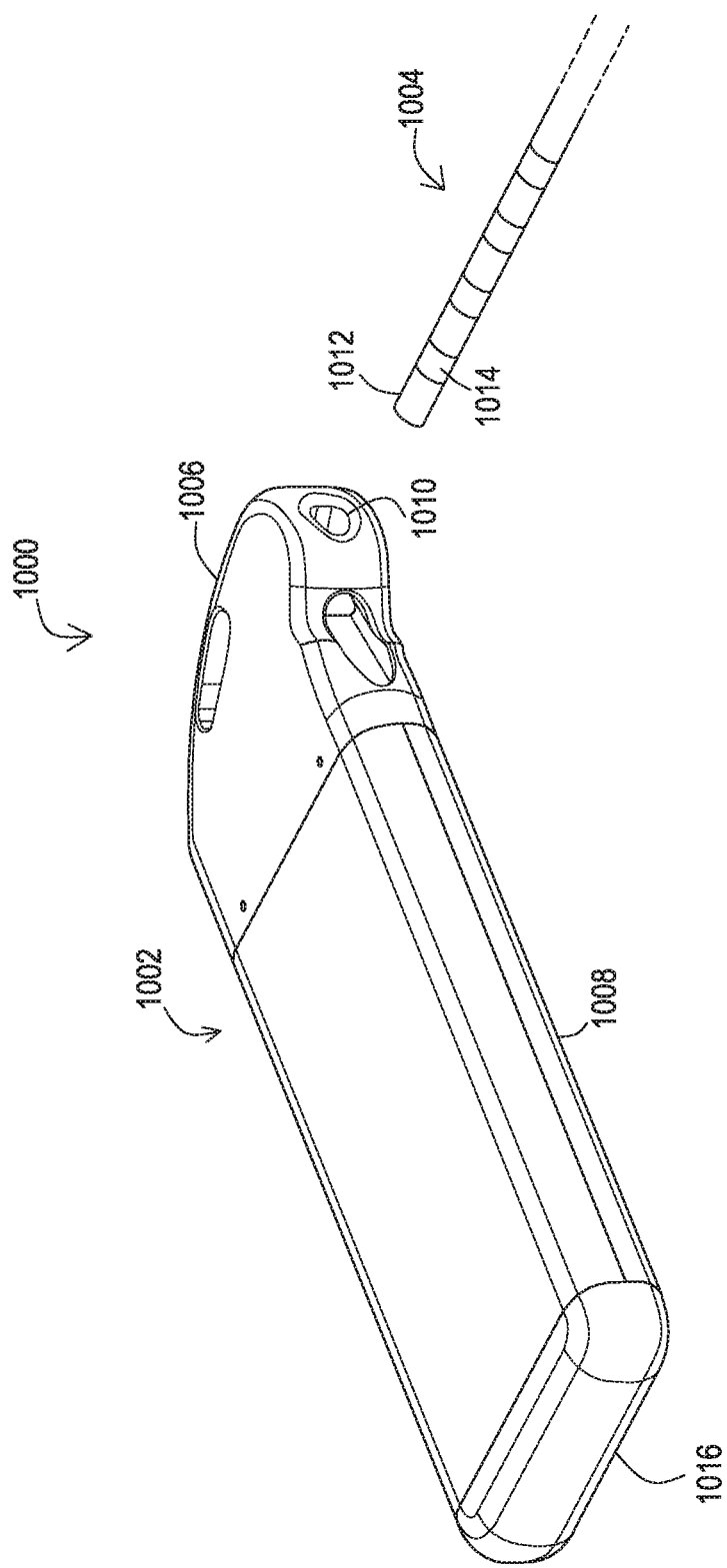
FIG. 9 shows another implantable medical system according to various embodiments.

Embodiments provide implantable medical devices that include various features related to the electrical connectivity of a connector enclosure assembly containing electrical connectors to a can that houses electrical circuitry. FIG. 9 shows an example of an IMB system 1100 that includes an IMB 1102 and an implantable medical lead 1104. The IMB 1102 may be of various types, such as a device for producing electrical stimulation and/or for sensing physiological signals for various medical applications such as neurological or cardiac therapy. The implantable medical lead 1104 includes a proximal end 1112 of a lead body where a series of electrical contacts 1114 are located. Each electrical contact has a corresponding conductor within the lead body that extends to a distal end (not shown) where a series of electrodes are present.

The implantable medical lead 1104 is implanted into the body with the distal end being routed to a desired location such that the electrodes contact the tissue of interest. The proximal end 1112 is inserted into a connector enclosure assembly 1106 of the IMB 1102 via an entryway 1110. Within the connector enclosure assembly 1106, electrical connectors make contact with each of the contacts 1114. Electrical circuitry within the can 1108 provides stimulation signals and/or monitors for sensed signals by being electrically connected to the connectors within the connector enclosure assembly 1106. The electrical circuitry is thereby also connected to the electrodes at the distal end of the implantable medical lead 1104 such that the stimulation signals may be provided to tissue at the electrodes and/or sensed signals may be obtained from the tissue.

Figure 10:
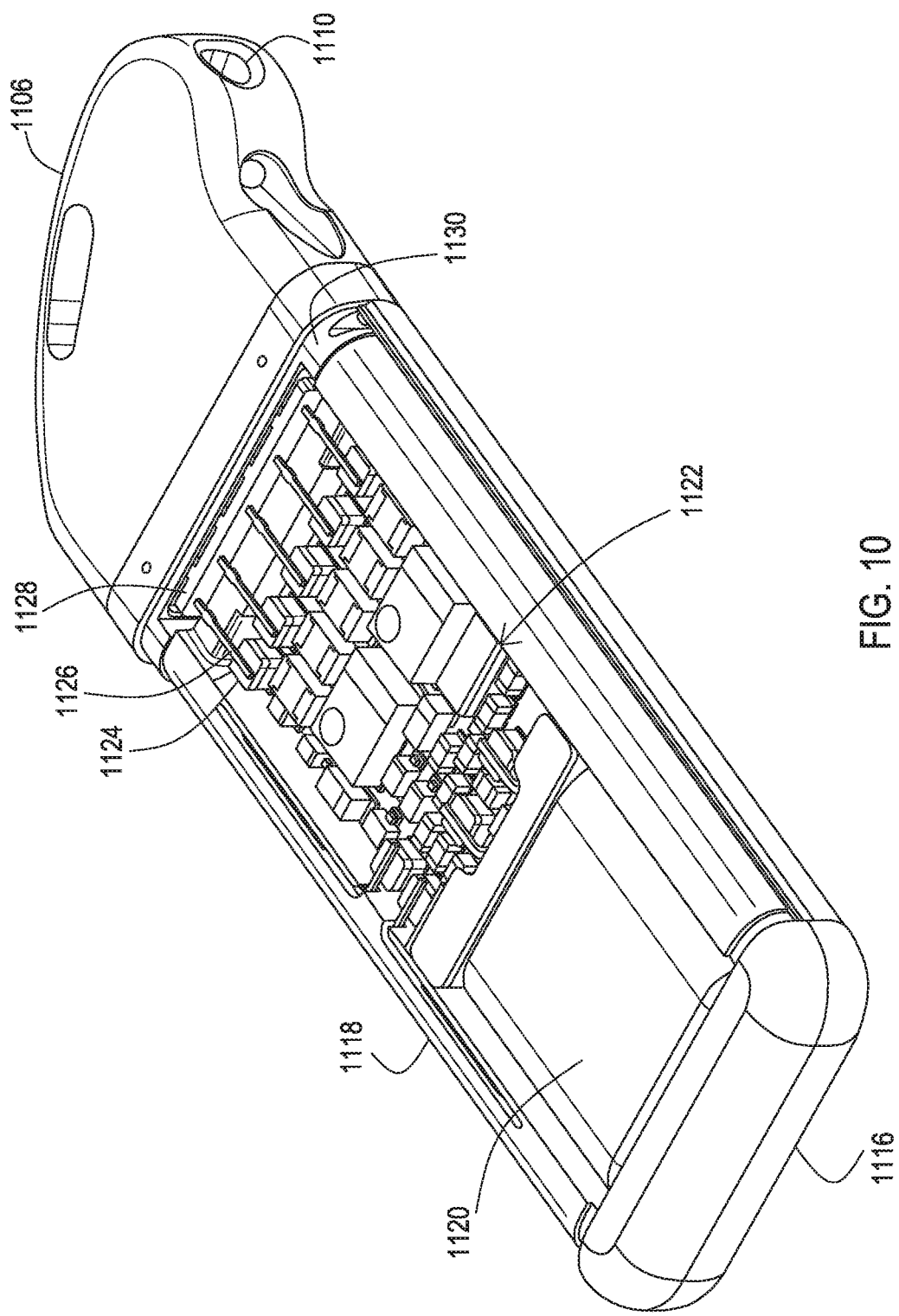
FIG. 10 shows an example of the implantable medical device of FIG. 9 with a portion of a can removed to reveal interior features.

In this particular example, the can 1108 relies on separate components to create a hermetically sealed enclosure for the electrical circuitry. Namely, the can 1108 relies on a bottom cap 1116 that may be welded in place or may be formed integrally with the can 1108 and relies on a base plate 1130 which is shown in FIG. 10 that is a component of the connector enclosure assembly 1106 in this example. During manufacturing, the connector enclosure assembly 1106 is joined to the can 1108 by the base plate 1130 being bonded such as by a weld to the top edge of the can 1108. The can 1108, bottom cap 1116, and the connector assembly 1106 including the base plate 1130 may be made of rigid biocompatible materials such as various grades of titanium.

FIG. 10 shows the IMD 1102 with one side of the can 1108 removed to reveal inner components. In this example, the IMD 1102 includes a battery 1120 and electrical circuitry 1122 housing within an isolation cup 1118. The isolation cup 1118 may securely hold the components within the can 1108 while isolating the components from contact with the can 1108. The isolation cup 1118 may be constructed of an insulator such as a liquid crystal polymer.

In this particular example, the electrical circuitry 1122 includes electrical contact pads 1124. Conductors 1126 that extend from the connector enclosure assembly 1106 align with and are bonded to the electrical contact pads 1124 such as by soldering or a spot weld or the like during assembly of the IIMD 102. As discussed in more detail below, these conductors 1126 provide electrical connectivity between the electrical circuitry 1122 and feed through pins, where the feedthrough pins provide electrical connectivity to the electrical connectors within the connector enclosure assembly 1106.

As the conductors 1126 extend from the feedthrough pins 1136 to the contact pads 1124 in this example, there is no need for a flexible circuit to provide the interconnection. Accordingly, the structure for interconnecting the flexible circuit to the feedthrough pins is omitted.

The conductors 1126 pass through a support body 1128 that is affixed to the underside of the base plate 1130. The support body 1128 holds the conductors in proper positioning for interconnection to the feedthrough pins of the connector enclosure assembly 1106 and also in proper position for bonding to the contact pads 1124 of the electrical circuitry 1122 within the can 1108. The support body 1128 is discussed in more detail below with reference to FIG. 18. A discussion of the assembly of the device 1102 is also discussed in more detail below.

Figure 11:
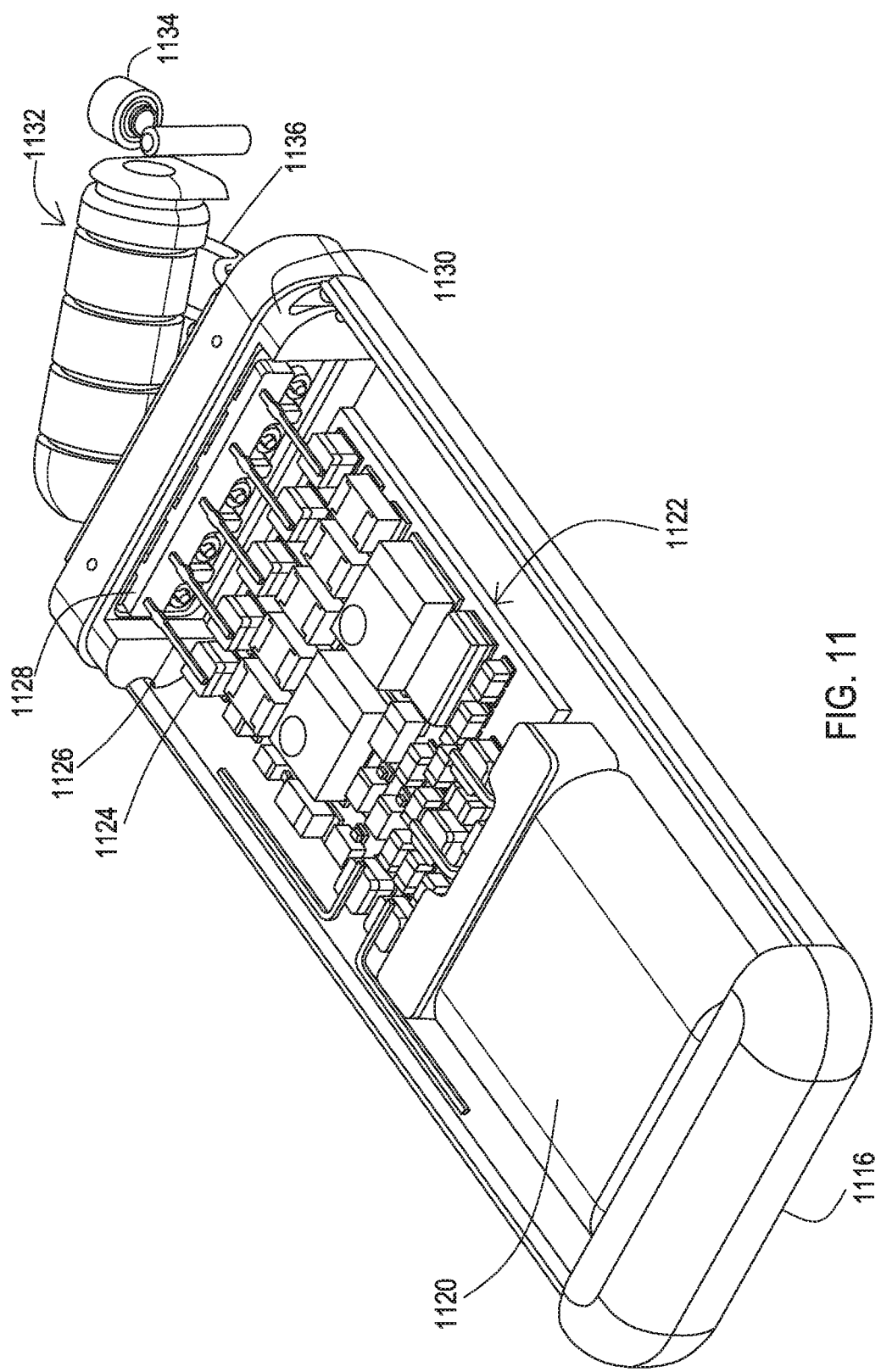
FIG. 11 shows the implantable medical device of FIG. 9 with a connector enclosure removed to further reveal interior features.

FIG. 11 shows the IMD 1102 with the connector enclosure removed to reveal the set of electrical connectors 1132, a set screw 1134, and feedthrough pins 1136. The connector enclosure which has been removed may be constructed of a polymer that is molded over the components shown in FIG. 11 or may be machined from a metal. For examples where the connector enclosure is machine from metal, passageways are include that allow the feedthrough pins 1136 to avoid contact with the metal enclosure walls, while the set of connectors 1132 are surrounded by an insulator separating the connectors 1132 from the metal enclosure walls. Furthermore, the interior of the connector enclosure may be filled with an insulator such as a silicone to further insulate conductors from the metal enclosure. In this particular example, the feedthrough pins extend up to the connectors 1132 and make electrical connection with the connectors 1132. It will be appreciated that in other examples, there may be an intervening electrically conductive structure to interconnect the feedthrough pins 1136 and the connectors 1132.

Figure 12:
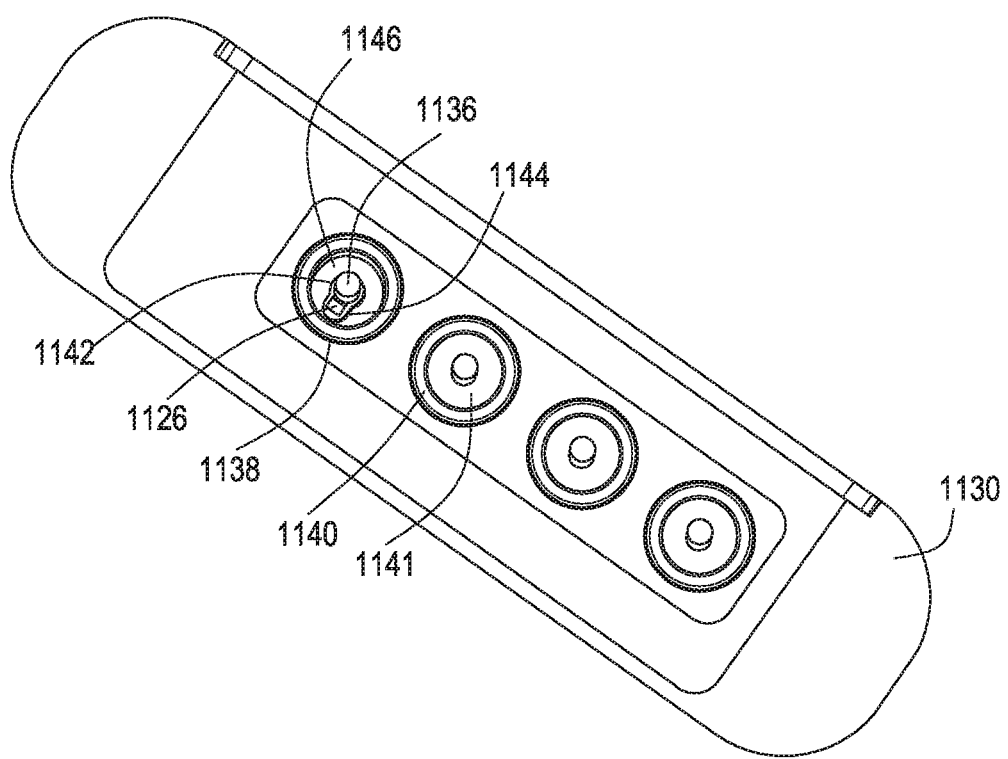
FIG. 12 shows a top view of a base plate and feedthrough pins of a connector enclosure assembly of the implantable medical device.

FIG. 12 shows a top view of the connector enclosure assembly with the connector enclosure and the connectors 1132 removed to reveal the top of the base plate 1130. The feedthrough pins 1136 can be seen rising from apertures 1138 within the base plate 1130. These apertures 1138 may include a ferrule 1140 or other similar structure that includes an insulator 1141 such as a nonconductive polymer which surrounds the feedthrough pin 1136 to support the feedthrough pin within the aperture 1138, create a seal between the feedthrough pin 1136 and the base plate 1130, and to isolate the feedthrough pin 1136 from contact with the base plate 1130.

In FIG. 12, the insulator material 1141 has been removed to reveal a filter capacitor 1146 that lies underneath the base plate 1130. The filter capacitor 1146 may be used to provide a filtered feedthrough by including capacitively coupled plates, where the interconnected feedthrough pin 1136 and conductor 1126 are capacitively coupled to ground to remove EMI signals from entering device. This capacitive coupling is discussed in more detail below.

The filter capacitor 1146 has an aperture 1142 that allows the feedthrough pin 1136 to pass through. In this particular example, the aperture 1142 also includes a region 1144 that allows the conductor 1126 to enter into the aperture 1142 such that the feedthrough pin 1136 and conductor 1126 are adjacent within the aperture 1142. In this particular example, the region is smaller than the portion of the aperture 1142 where the feedthrough pin 1136 passes such that the aperture 1142 has a keyhole shape.

The conductor 1126 and the feedthrough pin 1136 are in the vicinity of one another as well as in the vicinity of the aperture 1142. In this particular example, both the conductor 1126 and the feedthrough pin 1136 are present within the aperture 1142. Because the conductor 1126 and the feedthrough pin 1136 are in the vicinity of one another and in the vicinity of the aperture 1142, the conductor 1126 and the feedthrough pin 1136 may be bonded together as well as to the filter capacitor 1146 via a single bonding event, as opposed to a separate bonding event for the conductor and a separate bonding even for the feedthrough pin. Furthermore, the non-ground capacitor plates within the filter capacitor 1146 may be present at the non-ground aperture 1142 such that the bond may also occur with the non-ground capacitor plates as shown below in FIG. 16. Thus, a single bonding event creates an electrical connection among the feedthrough pin 1136, the conductor 1126, and the non-ground capacitor plate of the filter capacitor 1146 while creating a physical connection among feedthrough pin 1136, conductor 1126, and filter capacitor 1146.

The filter capacitor 1146 may be a ceramic material with conductive layer within to provide the capacitance. The aperture 1142 may have a border such as silver-palladium or Ni—Au plating or the like sputtered or otherwise attached to the ceramic about the aperture 1142 so that an electrically conductive bonding material may be used to bond the conductor 1126, the feedthrough pin 1136, and the filter capacitor 1146 together. For example, a solder joint 1148 may be created at the junction of the conductor 1126, the feedthrough pin 1136, and the filter capacitor 1146.

Figure 13A:
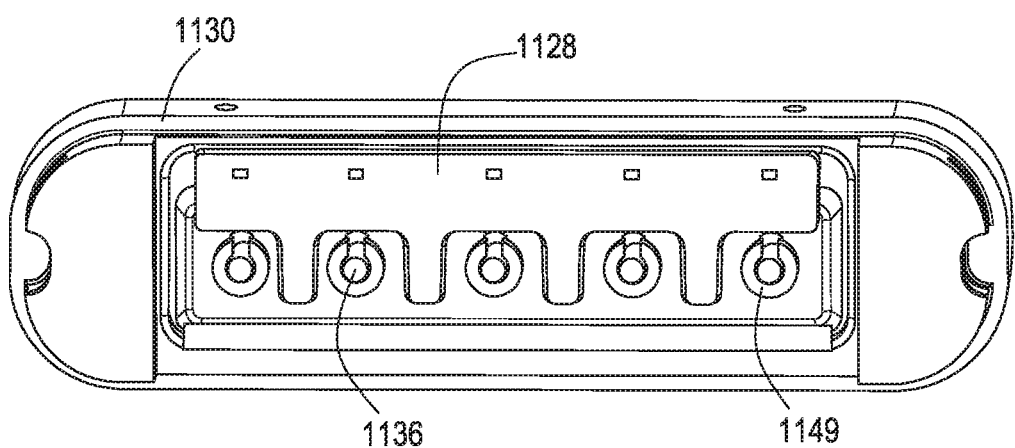
FIGS. 13A and 13B each show a bottom view of a base plate, feedthrough pins, and related conductors of a connector enclosure assembly of the implantable medical device of FIG. 9.
Figure 13B:
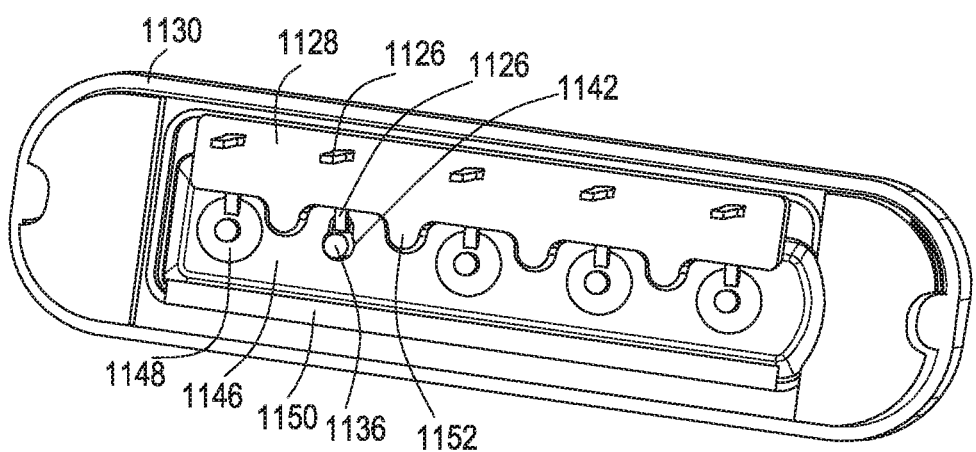

FIGS. 13A and 13B show the underside of the base plate 1130 with the connector enclosure assembly 1106 being free from the can 1108. A solder joint 1148 is present at the junction of a conductor, a pin, and the filter capacitor 1146. The filter capacitor 1146 itself may be mechanical and electrically bonded to the base plate 1130 via a bonding material 1150, such as solder where the edge of the filter capacitor has a metal sputtered in place or otherwise attached to the ceramic such that the bonding material 1150 such as solder bonds to the filter capacitor 1146 and to the base plate 1130.

FIG. 13A shows the underside prior to the bond being created among the feedthrough pin 1136, conductor 1126, and filter capacitor 1146. The bonding material, such as solder, may have a preformed shape. In this example, the preformed shape 1149 includes a split where the conductor 1126 is positioned prior to heating the preformed shape 1149. Upon heating, the preformed shape 1149 becomes the bonded material 1148 of FIG. 13B.

For purposes of illustration, in FIG. 13B the solder is omitted for one of the junctions of the feedthrough pin 1136 and conductor 1126 to reveal the keyhole shaped aperture 1142 with the feedthrough pin 1136 and conductor 1126 being present at the aperture 1142. FIG. 13B also shows one view of the alignment of the support body 1128 and the filter capacitor 1146. In this example, the support body 1128 includes protrusions 1152 that occur between each of the apertures 1142 of the filter capacitor 1146.

Figure 14:
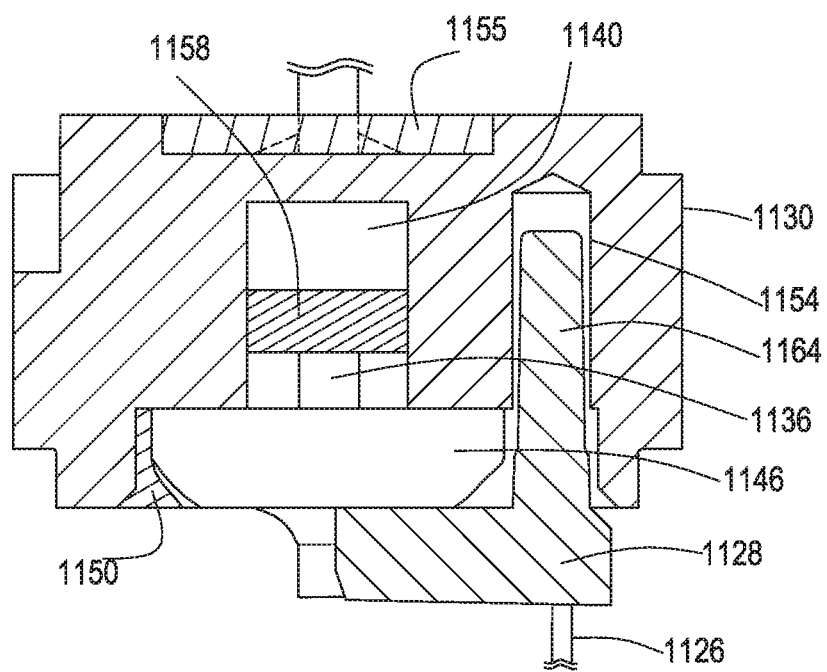
FIG. 14 shows a front-to-back cross-sectional view taken through the base plate to reveal a mounting post of a support body of the connector enclosure assembly.

FIG. 14 shows a cross-sectional view further illustrating the relationship of the support body 1128 to the filter capacitor 1146 and the base plate 1130. Here it can be seen that the support body 1128 of this example includes a mounting post 1164. The mounting post 1164 is press fit into a cavity 1154 within the base plate 1130. This press fit holds the support body 1128 in a fixed position with respect to the base plate 1130, and also provides additional support for the filter capacitor 1146 as the support body 1128 contacts the underside of the filter capacitor 1146.

FIG. 14 also shows the ferrule 1140 that separates the nonconductive polymer 1141 not shown in this view and the feedthrough pin 1136 from the base plate 1130. FIG. 14 also shows a separate insulator 1158 that is present beneath the ferrule 1140 and that is located between the feedthrough pin 1136 and the base plate 1130. Additionally, a coating of a nonconductive material 1155 such as a medical adhesive can be seen atop the base plate 1130 covering the area where the feedthrough pins 1136 pass into the base plate 1130.

Figure 15:
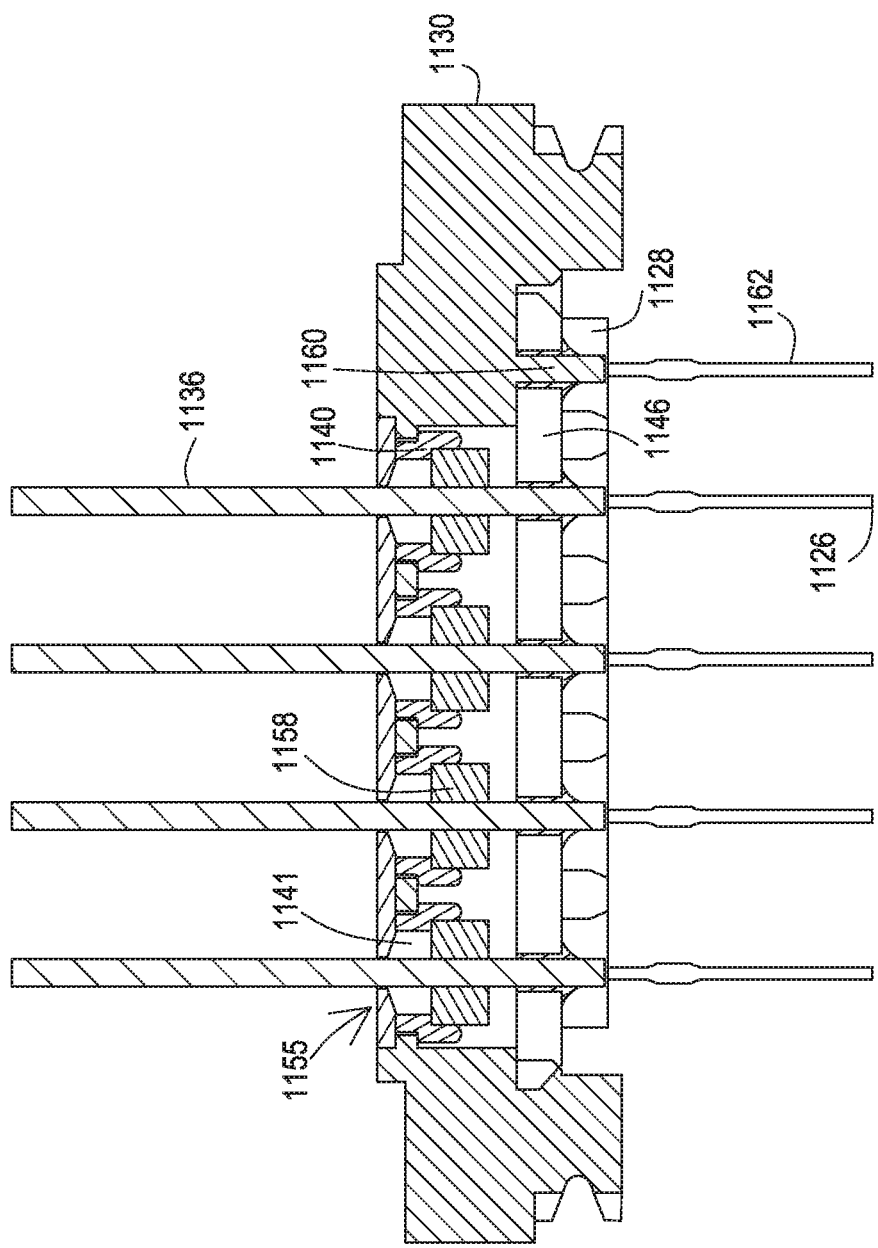
FIG. 15 shows a side-to-side cross-sectional view taken through the base plate to reveal an integral ground pin of the base plate as well as the feedthrough pins and related conductors of the support body.

FIG. 15 shows another cross-sectional view of the base plate 1130 and the filter capacitor 1146. FIG. 15 shows another view of the relationship between the medical adhesive 1155, the ferrule 1140, the nonconductive polymer 1141, the insulator 1158, and the feedthrough pin 1136. This view also reveals that the base plate 1130 of this particular example includes an integral ground pin 1160. This integral ground pin 1160 may be machined as a feature of the base plate 1130. As an alternative, a ground pin 1160 could be welded or otherwise attached to the base plate 1130.

A ground conductor 1162 is interconnected within the ground pin 1160 via an electrically conductive bond at a ground aperture of the filter capacitor 1146. Thus, the electrically circuitry 1122 has a ground to the base plate 1130 which will ultimately be electrically connected to the can 1108 upon welding of the base plate 1130 to the can 1108. Furthermore, the ground aperture of the filter capacitor 1146 may include the ground plates of the capacitive coupling present within the filter capacitor 1146 such that the electrically conductive bond also occurs with the ground plates, which is discussed in more detail below with reference to FIG. 17. Therefore, in a single bonding event, an electrically conductive bond may occur among the ground pin 1160, a ground conductor 1162, and the ground capacitor plate of the filter capacitor 1146 while a physical bond may also occur among the ground pin 1160, the ground conductor 1162, and the filter capacitor 1146.

Figure 16:
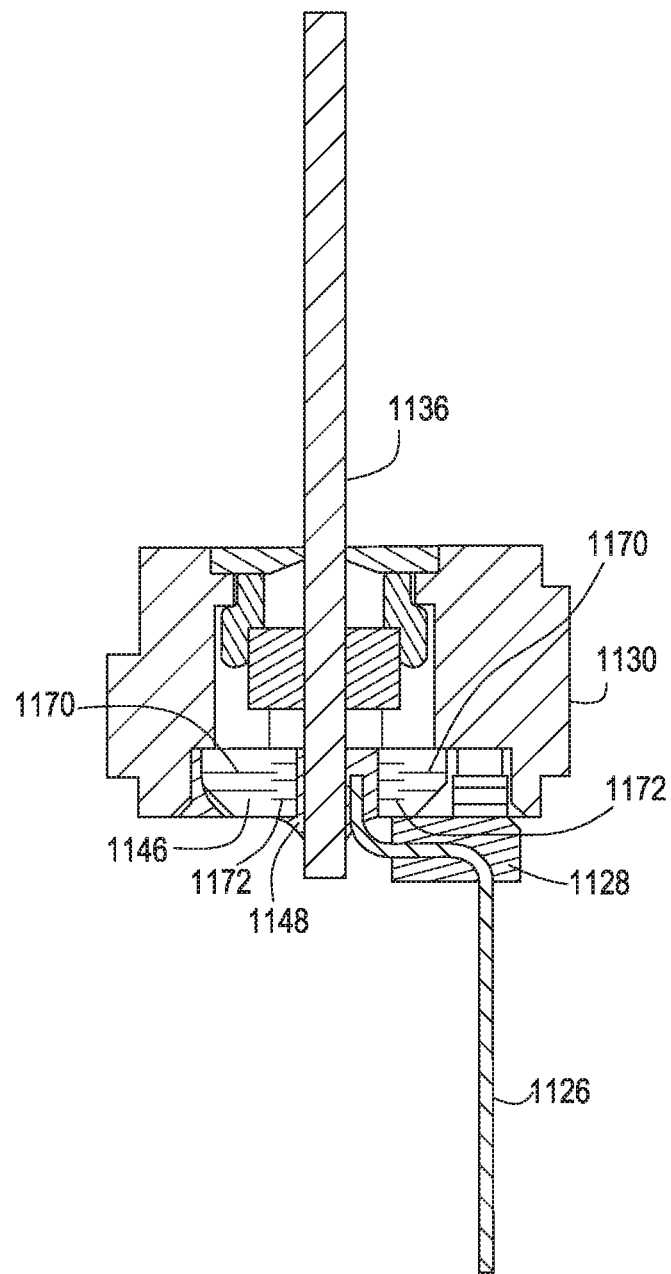
FIG. 16 shows a front-to-back cross-sectional view taken through the base plate to reveal the interconnection of the feedthrough pin, related conductor, and filter capacitor.

FIG. 16 shows another cross-sectional view which illustrates an example where the feedthrough pin 1136 and the conductor 1126 are both present within the aperture 1142 of the filter capacitor 1146. Here, the non-ground capacitor plates 1172 and the ground capacitor plates 1170 can be seen within the filter capacitor 1146, and the electrically conductive bond material 1148 such as solder can also be seen filling the aperture and creating the electrical connection between the feedthrough pin 1136, the conductor 1126, and the non-ground capacitor plates 1172. As can also be seen the ground capacitor plates 1170 are electrically connected to the base plate 1130.

Figure 17:
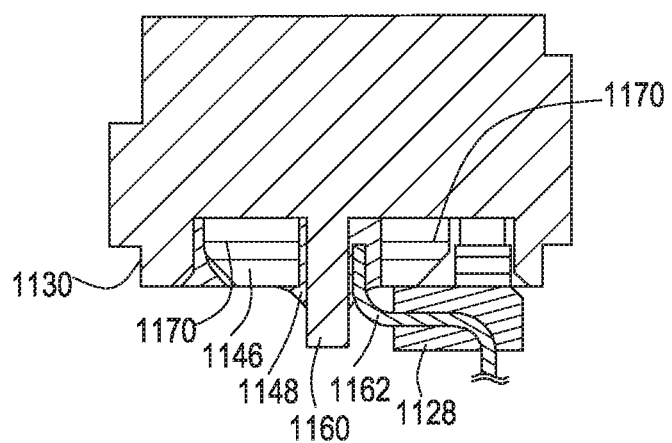
FIG. 17 shows a front-to-back cross-sectional view taken through the base plate to reveal the interconnection of the integral ground pin, related conductor, and filter capacitor.

FIG. 17 shows another cross-sectional view which reveals details of the ground aperture of the filter capacitor 1146. Here it can be seen that the ground plates 1170 are present at the ground aperture of the filter capacitor 1146 such that the ground pin 1160, ground conductor 1162, and the ground plates 1170 are electrically interconnected via the electrically conductive bonding material 1148. In this case, there is a direct ground path from the electrical circuitry 1122 to the ground plates 1170 through this junction established by the electrically conductive bonding material 1148.

Figure 18:
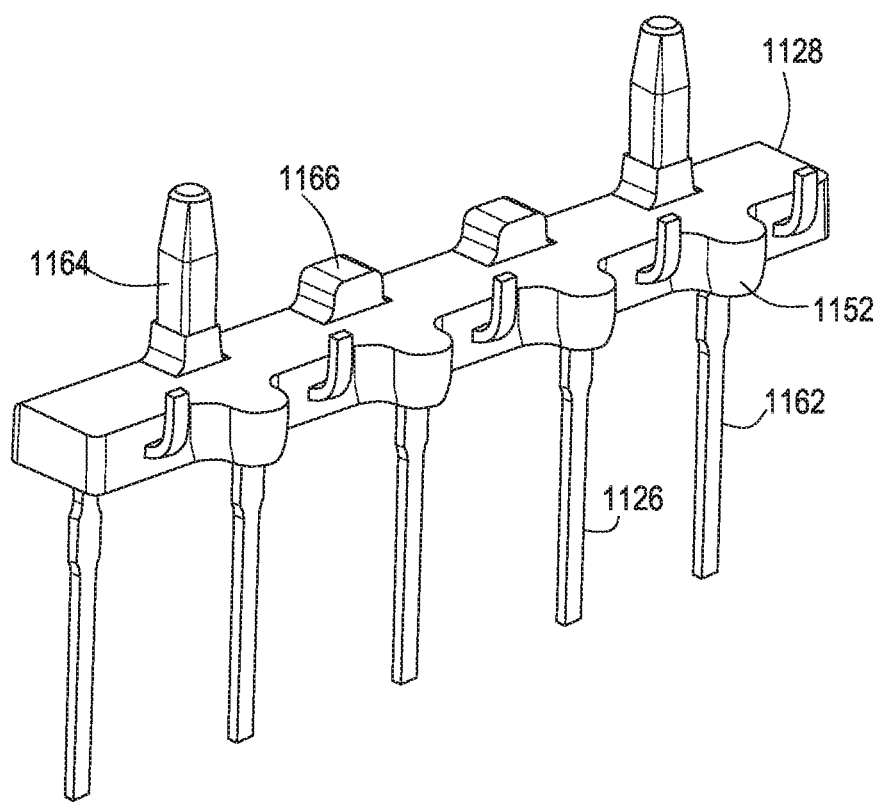
FIG. 18 shows the support body and conductors that pass therethrough.

FIG. 18 shows details of the support body 1128 and conductors 1126, 1162. Here it can be seen that the conductors pass through the support body 1128, such as into one side and out another. In this case, the conductors 1126, 1162 pass through a bottom side and out a front side but it will be appreciated that the conductors 1126, 1162 could pass through other sides of the support body 1128. As the support body 1128 contains the conductors, the support body 1128 is constructed of an insulator such as polyether ether ketone (PEEK).

The support body 1128 includes the posts 1164 as well as protrusions 1166 that abut the base plate 1130 to create proper spacing between the support body 1128 and the base plate 1130 where the filter capacitor 1146 resides. The support body also includes the protrusions 1152 which properly position the support body 1128 by abutting the filter capacitor 1146 to align the interfacing surfaces.

Figure 19:
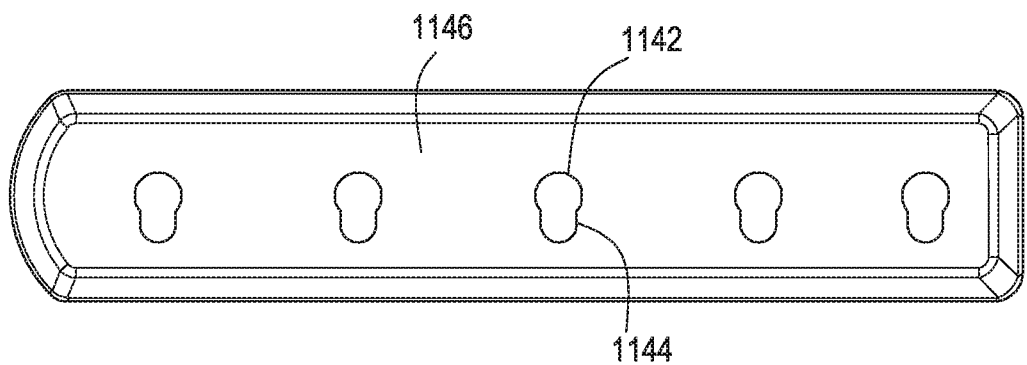
FIG. 19 shows the filter capacitor and related apertures.

FIG. 19 shows the filer capacitor 1146. This view further illustrates the asymmetric shape of this particular example as discussed above. This view also further illustrates the apertures 1142 of this example, and particularly the keyhole shape of the apertures 1142 having the smaller diameter portion 1144.

Figure 20:
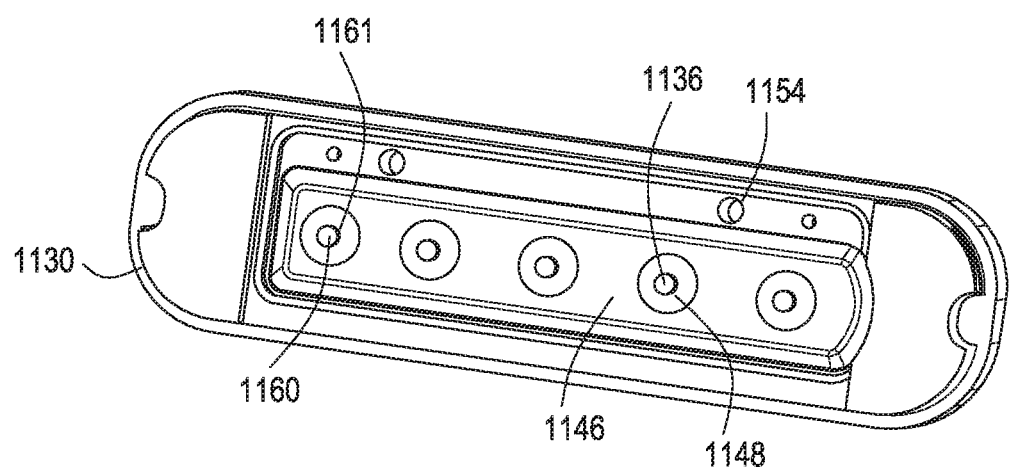
FIG. 20 shows a bottom view of the connector enclosure assembly with the support body removed to reveal the filter cap.

FIG. 20 shows the underside of the base plate 1130 and the filter capacitor 1146 with the support body 1128 omitted for purposes of illustration. Here, the cavities 1154 in the base plate 1130 can be seen that receive the posts 1164 of the support body 1128. Another feature that can be seen in FIG. 20 is the asymmetrical shape of the filter capacitor 1146 in this example, where one end is square and the opposite end is curved outwardly. The base plate 1130 has a matching asymmetrical recess which prevents the filter capacitor 1146 from being inserted in the wrong orientation. For embodiments where one of the apertures of the filter capacitor 1146 is a ground aperture 1161 where the ground plates 1170 are present, this is significant because this prevents the ground aperture 1161 from being aligned with a feedthrough pin 1136 because the ground pin 1160 should be present in the ground aperture 1161 rather than a feedthrough pin 1136.

Figure 21:
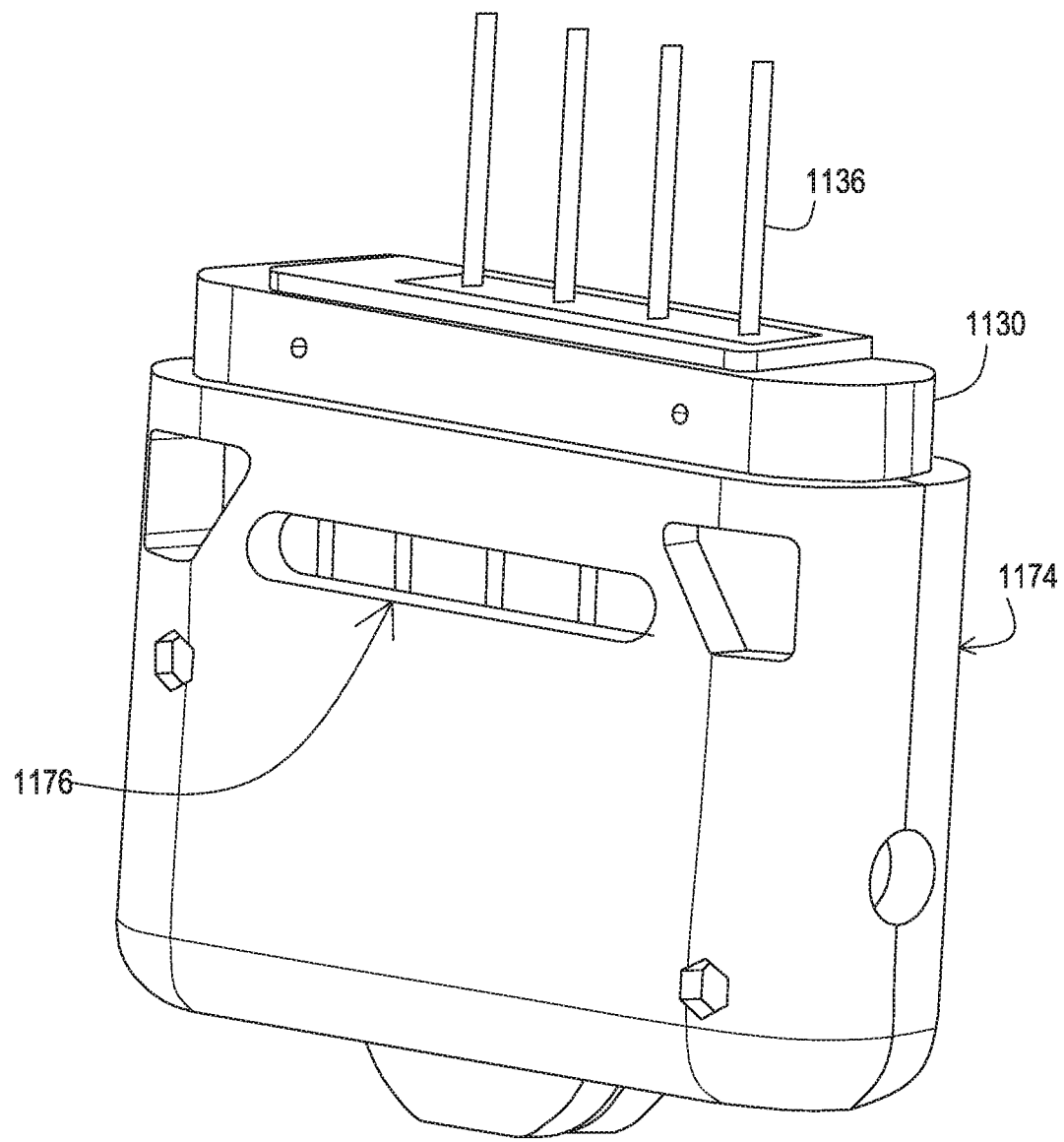
FIG. 21 shows a view of the base plate portion of the connector enclosure assembly with a protective body attached thereto.

FIG. 21 shows a protective body 1174 that is attached to a partial connector enclosure assembly that includes the base plate 1130 and the feedthrough pins 1136, as well as the filter capacitor 1146, support body 1128, and conductors 1126 within the protective body 1174. The protective body 1174 protects the underside of the base plate 1130, particularly the exposed conductors 1126 that are intended to extend into the can of the IMD 1102, during the construction, testing, transporting, and storage of the connector enclosure assembly 1106. The protective body 1174 may be constructed of various rigid materials but where electrical testing is desired, the protective body 1174 is constructed of an insulator such as liquid crystal polymer to avoid short circuiting across the conductors 1126.

Figure 22:
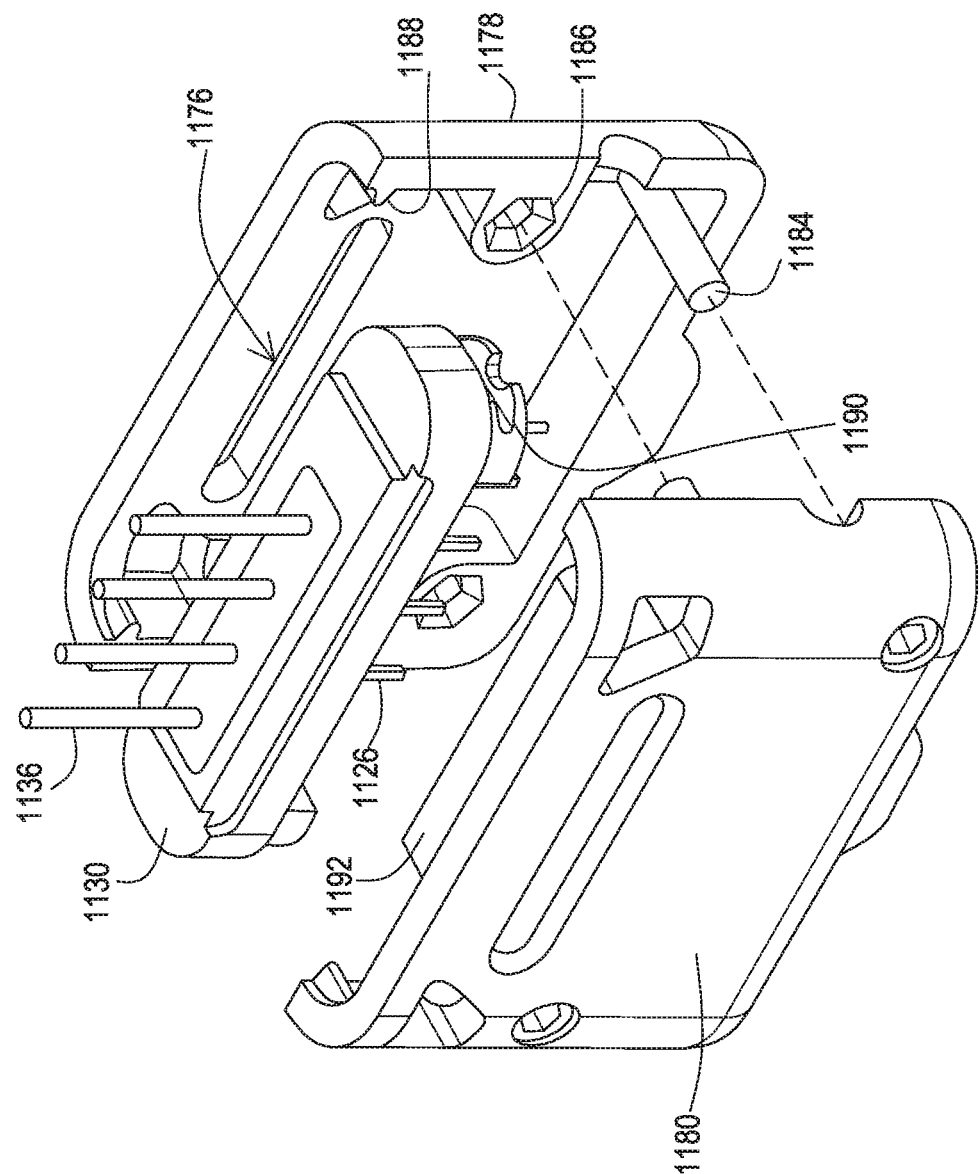
FIG. 22 shows an exploded view of the protective body.

The protective body 1174 includes a window 1176 that exposes the conductors 1126 so that electrical connection may be made to test the electrical pathway between the conductors 1126 and the individual electrical connectors 1132 as shown in FIG. 11. As shown in FIG. 22, the protective body 1174 may include two halves, a half 1180 and another half 1178. In this example, a window 1176 exists within the half 1174 for access to the conductors 1126.

The protective body 1174 may also include features that allow the two halves 1178, 1180 to be joined together while engaging the base plate 1130. For instance, posts 1184 and receptacles 1186 may be provided where the posts are press fit into the receptacles as a flange 1188 of each half slides into place within a groove 1190 on the base plate 1130. This locks the two halves 1178, 1180 together while locking the body 1174 to the base plate 1130.

Figure 23:
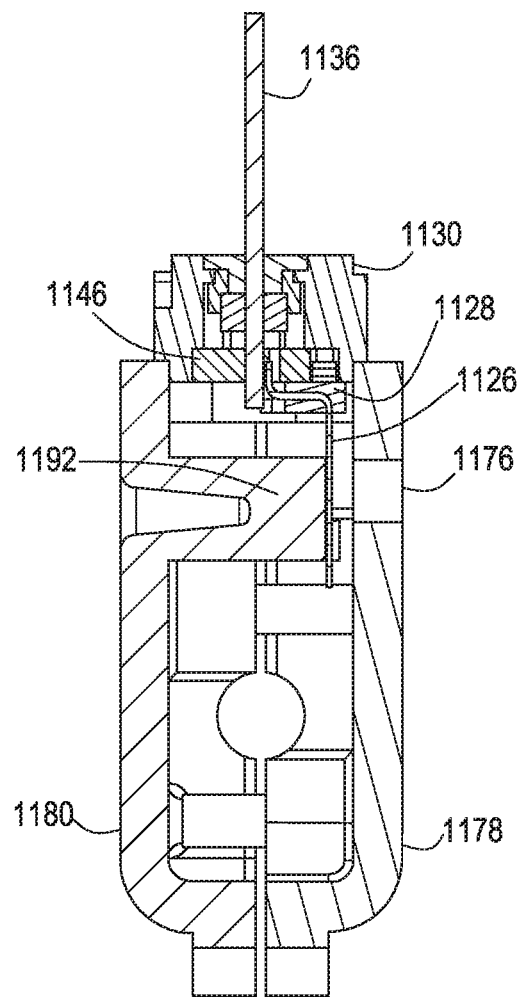
FIG. 23 shows a front-to-back cross-sectional view of the base plate and protection body.

FIG. 23 shows a cross-sectional view which shows the relationship of an extended support 1192 to the conductor 1126. The support 1192 extends over to the conductor 1126 so as to provide a stop against movement of the conductor 1126. Thus, the conductor 1126 is protected from excessive movement that could bend or break the conductor 1126 such as during assembly, testing, transport, and/or storage.

Figure 24:
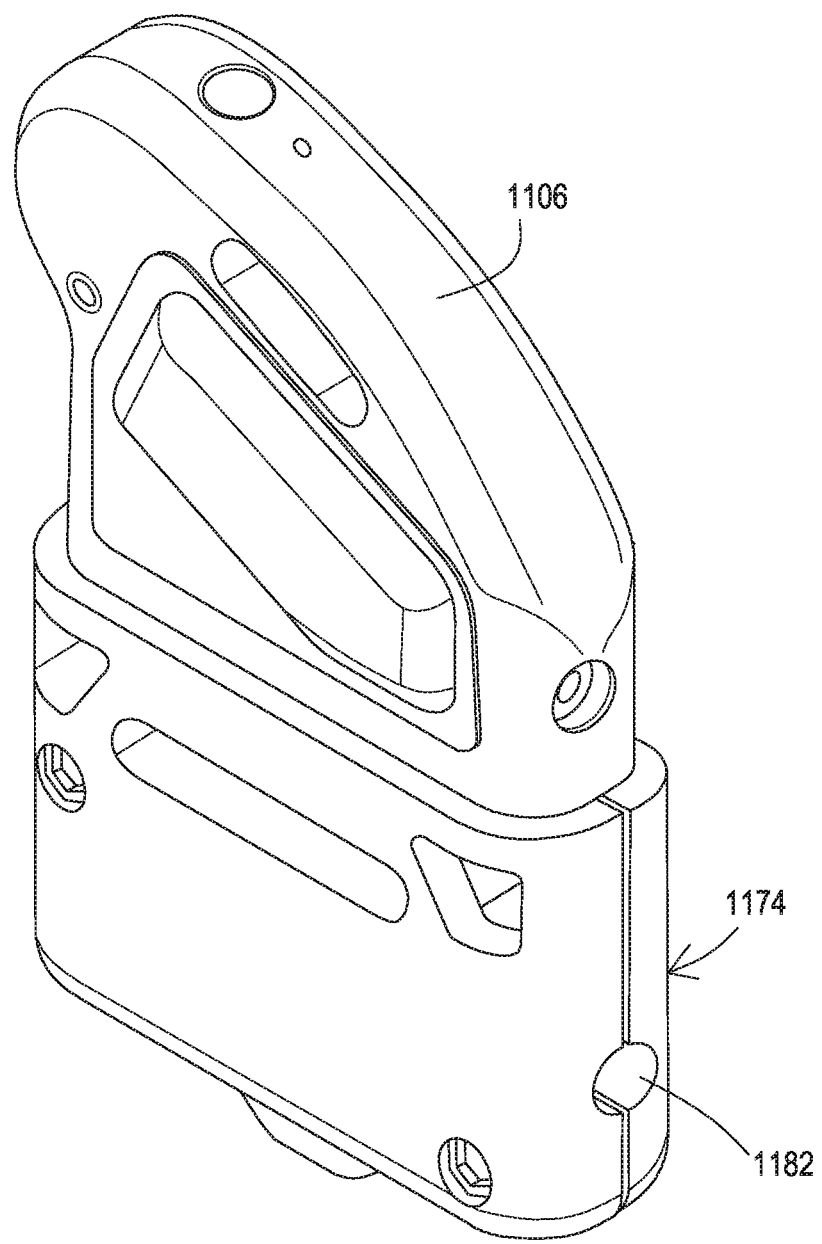
FIG. 24 shows a view of the connector enclosure assembly with the protective body attached thereto.

FIG. 24 shows the completed connector enclosure assembly 1106 with the protective body 1174 being attached to the base plate 1130 of the connector enclosure assembly 1106. At this point, the connector enclosure assembly 1106 is ready for testing, transport, and storage while the can portion of the IMD 1102 is being readied for attachment to the connector enclosure assembly 1106. When the time arrives for attachment, the protective cover 1174 is broken open using the holes 1182 that are on both sides of the protector halves 1178 & 1180. The assembly process of the IMD 1102 then proceeds.

One manner of assembling the IMD 1102 that includes the features discussed above follows. It will be appreciated that this manner of assembly is for illustrative purposes and that other manners of assembling the IMD 1102 are also possible. Initially in this example, the inner region where the feedthrough apertures 1138 are located is welded in place to an outer structure of the baseplate to complete the baseplate assembly 1130. The inner region contains the feedthrough pins 1136 passing through the ferrules 1140 filled with the nonconductive polymer 1141 and with the insulator 1158 being located underneath the ferrule 1140.

The filter capacitor 1146 is then inserted with each feedthrough pin 1136 passing through an aperture 1142. The support body 1128 with the conductors 1126 present therein is then positioned so that each conductor 1126 enters the region 1144 of the aperture 1142. The support body 1148 is then pressed into place such that the mounting posts 1164 firmly lock into the cavities 1154 of the baseplate 1130.

At this point, the feedthrough pins 1136, conductors 1126, and filter capacitor 1146 may be bonded by placing the solder split performs 1149 in place as shown in FIG. 13A. The filter capacitor 1146 may also be bonded to the baseplate 1130 at this time by placing a solder wire along the edge of the filter capacitor 1146 between the filter capacitor 1146 and the base plate 1130. The solder wire 1150 and solder split performs 1149 are then reflowed to complete the partial connector enclosure assembly.

The protective cover 1174 is then installed as shown in FIG. 21. Thermal, shock, and electrical testing may then be performed. The partial connector enclosure assembly is then ready for further assembly and may be transported and/or stored prior to the time to complete the assembly.

At the next step, the nonconductive polymer 1141 is added to the ferrules 1140 and then the medical adhesive 1155 is applied to the top of the baseplate 1130. The feedthrough pins 1136 are formed as necessary to be in position to contact the electrical connectors 1132. The pre-assembled set of electrical connectors 1136, such as a Bal Seal® stack is then placed against the feedthrough pins 1136 where they are then mechanically and electrically interconnected.

A top portion of the connector enclosure 1106 is then placed onto the baseplate 1130 and set of connectors 1132. The set screw 1134 is inserted into position within the top portion of the connector enclosure 1106. A cover plate of the connector enclosure 1106 that covers an open side of the top portion of the connector enclosure 1106 is put in position on the top portion and against the baseplate 1130. The top portion, cover plate, and the baseplate 1130 are then seam welded, and the cavity within the connector enclosure 1106 is filled with a non-conductive polymer by injection molding. At this point, the connector enclosure 1106 is ready for final assembly of the IMD 1102.

During final assembly, the isolation cup 1118 is placed into the bottom half of the can 108 as shown in FIG. 10. The electrical circuitry 1122 is then placed within the isolation cup 1118, and the battery 1120 is also positioned within the isolation cup 1118.

The protective cover 1174 is broken open to allow the connector enclosure assembly 1106 to be removed from the protective cover 1174. The connector enclosure assembly 1106 is then placed over the bottom half of the can 1108 and the conductors 1126 are mechanically and electrically connected to the electrical pads 1124.

The bottom cap 1116 is then added to the bottom half of the can 1108. The top half of the can 1108 is then placed into position relative to the bottom half. The interfaces of the two halves of the can 1108, the bottom cap 1116, and the baseplate 1130 of the connector assembly 1106 are seam welded to complete the assembly of the IMD 1102.

Figure 25:
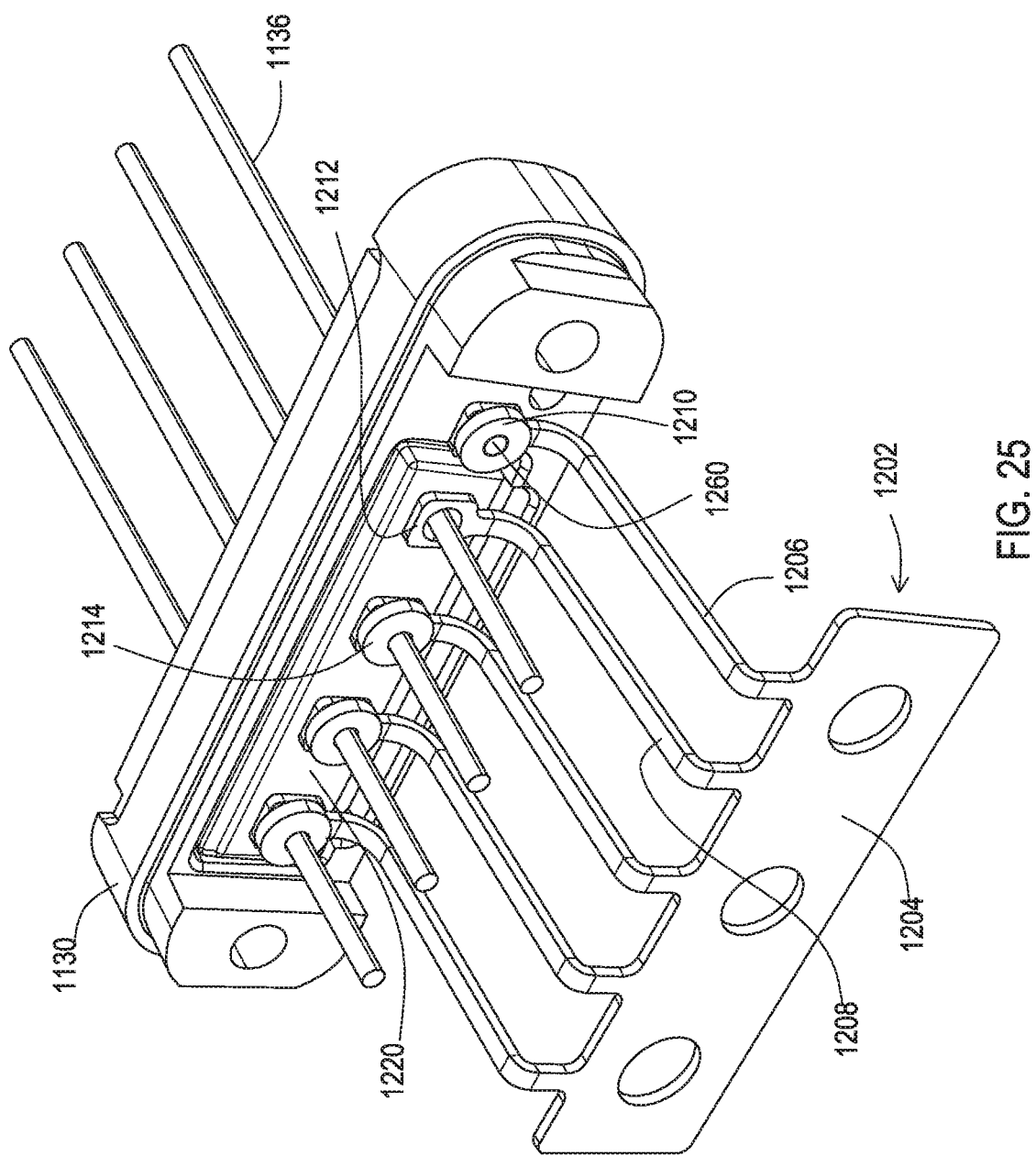
FIG. 25 shows another embodiment of an interconnection of a filtered feedthrough.

FIG. 25 shows another embodiment of an interconnection of a filtered feedthrough. Here the feedthrough pins 1136 pass through apertures in the baseplate 1130 and through a filter capacitor 1220 as discussed for the prior embodiments. However, in this embodiment, the interconnection of the feedthrough pins 1136 to the pads on the hybrid of the circuitry within the can is ultimately provided by conductors 1206, 1208. In this particular embodiment, these conductors 1206, 1208 are held in a fixed position with respect to one another prior to being installed by being formed together as an integral conductor unit 1202 where each conductor 1206, 1208 extends from a common tab 1204. The integral conductor unit 1202 may be constructed of materials such as titanium, nickel, niobium, tantalum, platinum, MP35N® alloy, or other alloys thereof. Furthermore, the integral conductor unit 1202 may include an outer layer that is plated or sputtered with material such as noble metals like gold or platinum to allow solder wetting to the conductor 1206, 1208 to occur during the soldering process.

The common tab 1204 allows the integral conductor unit 1202 to be easily grasped and positioned during assembly of the structure shown in FIG. 25 while the conductors 1206, 1208 maintain their relative spacing and orientation. Each conductor 1206, 1208 extends from the common tab 1204 at the proper spacing relative to the feedthrough pins 1136 such that the conductors 1206, 1208 are more easily aligned and mated to the corresponding feedthrough pins 1136.

In this particular embodiment, the ends of the conductors 1206, 1208 opposite the common tab 1204 include annular rings such as the annular ring 1212 revealed for the conductor 1208. The feedthrough pins 1136 pass through the openings of the annular rings 1212. The annular rings are then secured to the feedthrough pins 1136. In the case of the ground conductor 1206, the annular ring is secured to a ground pin 1260 of the baseplate 1130. Thereafter, the common tab 1204 is removed from the conductors 1206, 1208 such as by cutting or breaking the conductors 1206, 1208 in vicinity of the common tab 1204. For instance, the conductors 1206, 1208 may be formed with a thinner section near the common tab 1204 which provides a weak area that facilities the cut or break.

There may be several ways to secure the conductors 1206, 1208 to the ground pin 1260 or feedthrough pins 1136. For instance, in some embodiments, the conductors 1206, 1208 may be soldered to the respective pin. As shown in FIG. 25, a pre-formed solder washer 1210, 1214 may be positioned about the pin and onto the annular ring and then reflowed to create a bond that forms the physical and electrical coupling of the conductors 1206, 1208 to the pins. The solder washer for the annular ring 1212 has been omitted from FIG. 25 for purposes of illustrating the annular ring but would be included to provide the bond.

Figure 26:
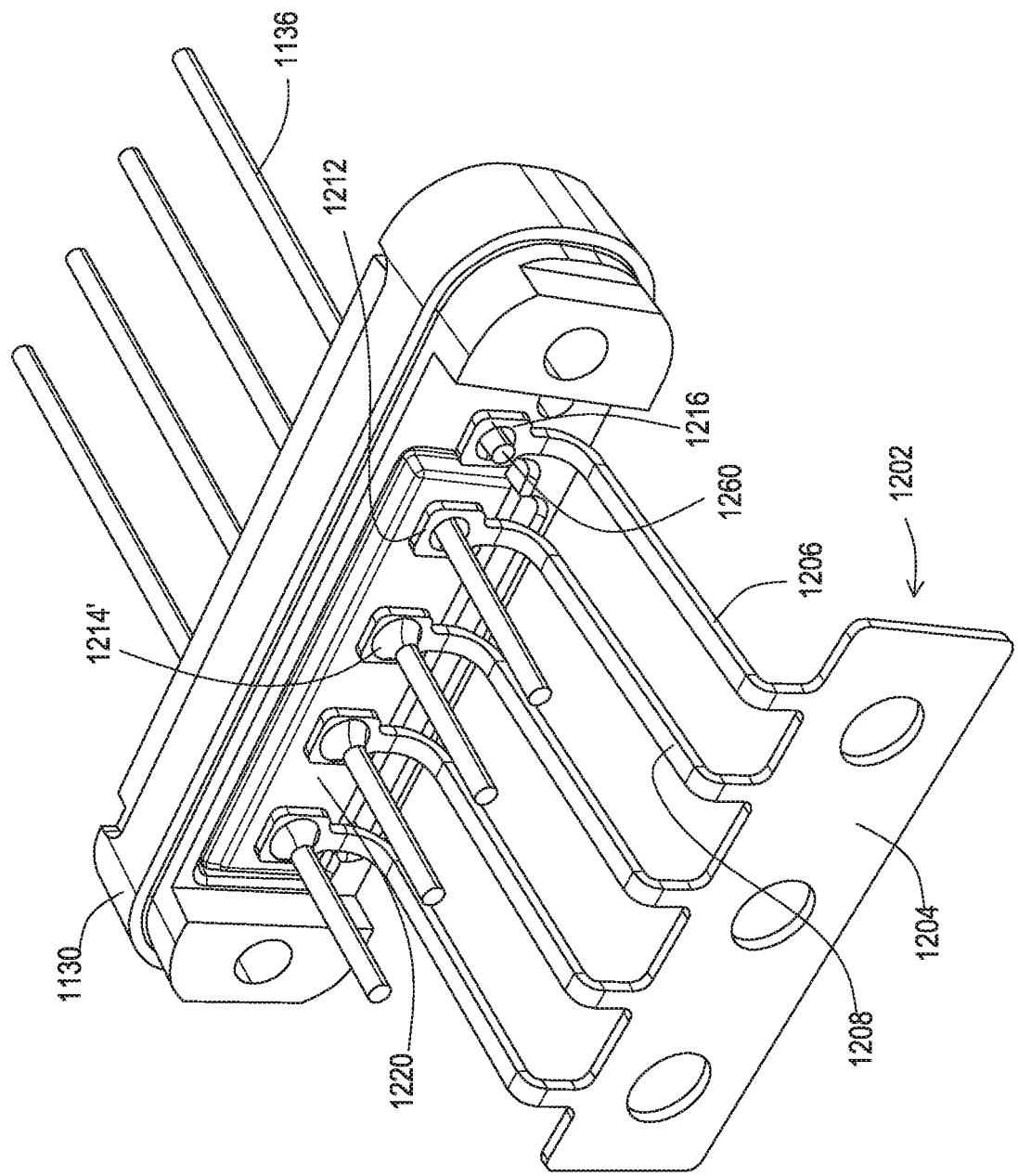
FIG. 26 shows the interconnection of some of the conductors to some of the feedthrough pins of the embodiment of FIG. 25.

FIG. 26 shows the interconnection of some of the conductors to some of the feedthrough pins 1136 once the solder has been reflowed to create the bond 1214'. FIG. 26 also omits the washer 1210 for the ground pin 1260 to more clearly illustrate the ground pin 1260 in relation to the annular ring 1216 of the ground conductor 1206. The reflowed solder 1214' of FIG. 26 also flows into the opening of the filter capacitor 1220 to create an electrical coupling of the feedthrough pin 1136 to a capacitor plate within the filter capacitor 1220. While FIG. 26 shows the feedthrough pins 1136 as extending well beyond the annular rings 1212, it will be appreciated that the feedthrough pins 1136 may be trimmed to the appropriate length before or after the soldering has occurred in order to achieve the final version shown in FIG. 29 which is discussed below.

Some embodiments of the annular rings 1212 may include extensions and the filter capacitor 1220 may include keyhole shaped openings like that of FIGS. 13B and 19 such that the extensions of the annular rings 1212 enter the keyhole area and are further soldered to the pin and capacitor plate. Likewise, for the embodiments discussed above with respect to FIGS. 13B and 18, those conductors 1126, 1162 may include annular rings that are positioned about the feedthrough pins as shown in FIGS. 25 and 26.

Figure 27:
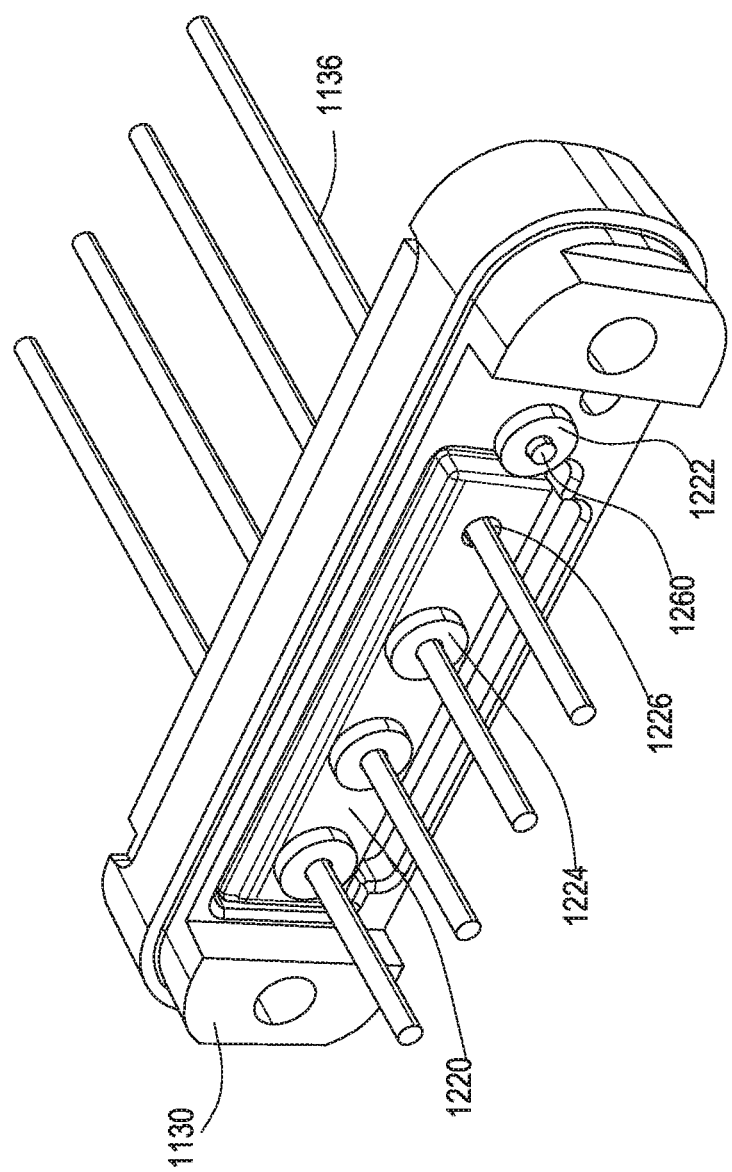
FIG. 27 shows an alternative manner of securing conductors to the pins.
Figure 28:
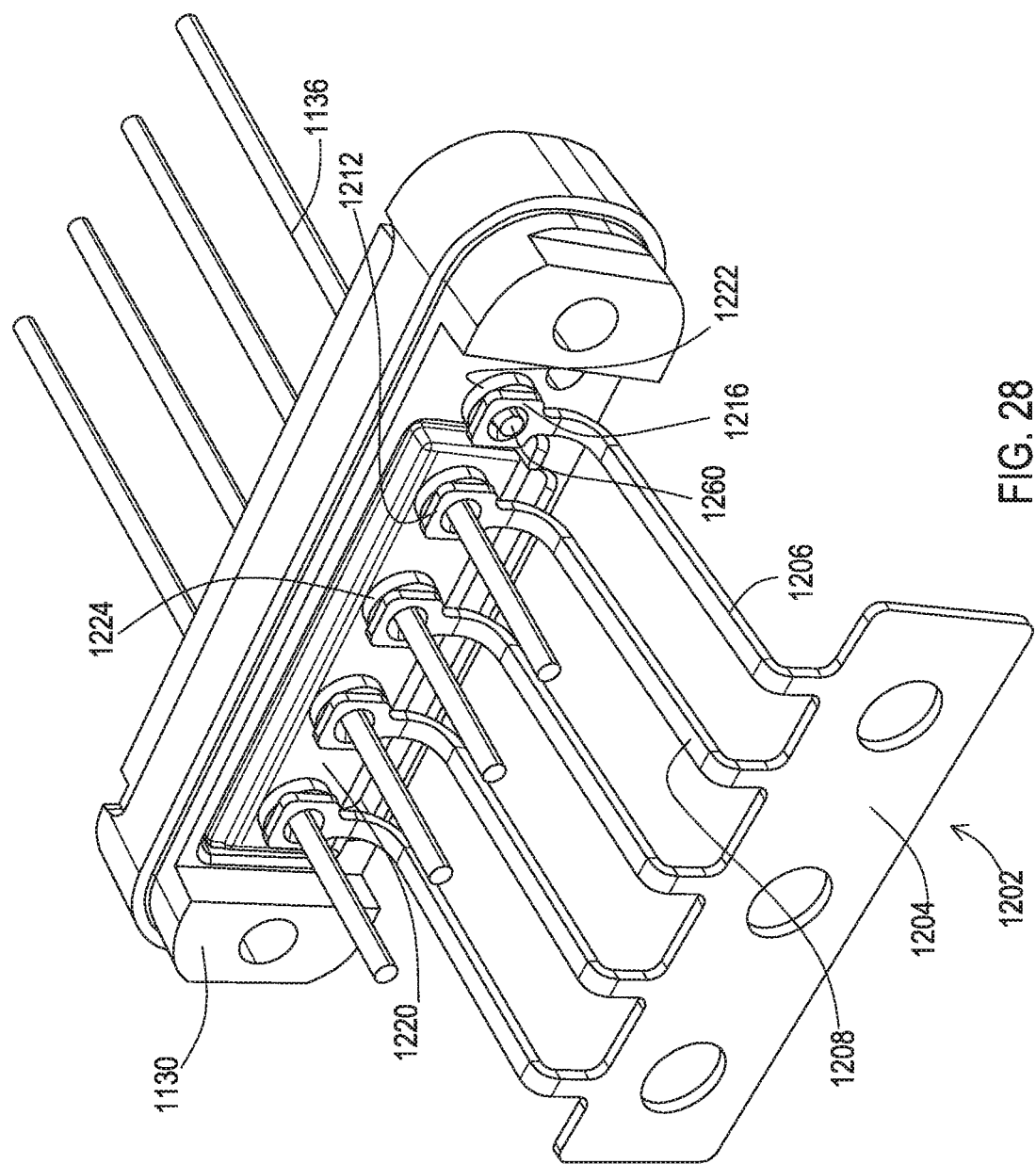
FIG. 28 shows annular rings are welded to the pins.

An alternative manner of securing the conductors 1206, 1208 to the pins is shown in FIG. 27. Here, the bond of the conductors 1206, 1208 to the pins 1260, 1136 is created by welding. In order to protect the filter capacitor 1220, protective washers 1222, 1224 are placed about the ground pin 1260 and feedthrough pins 1136, respectively. These protective washers may be constructed of a material such as alumina or glass to create an effective barrier. However, prior to installation of the washers, the feedthrough pins 1136 are soldered to the capacitive plates of the filter capacitor 1220 by flowing solder into the openings 1226 of the filter capacitor 1220. Then, the protective washers 1222, 1224 are put in place, followed by placement of the annular rings of the conductors 1206, 1208 about the pins 1260, 1136. The annular rings are then welded to the pins 1260, 1136. This configuration is illustrated in FIG. 28. While FIG. 28 shows the feedthrough pins 1136 as extending well beyond the annular rings 1212, it will be appreciated that the feedthrough pins 1136 may be trimmed to the appropriate length before welding has occurred in order to achieve the final version like that shown in FIG. 31 which is discussed below.

Figure 29:
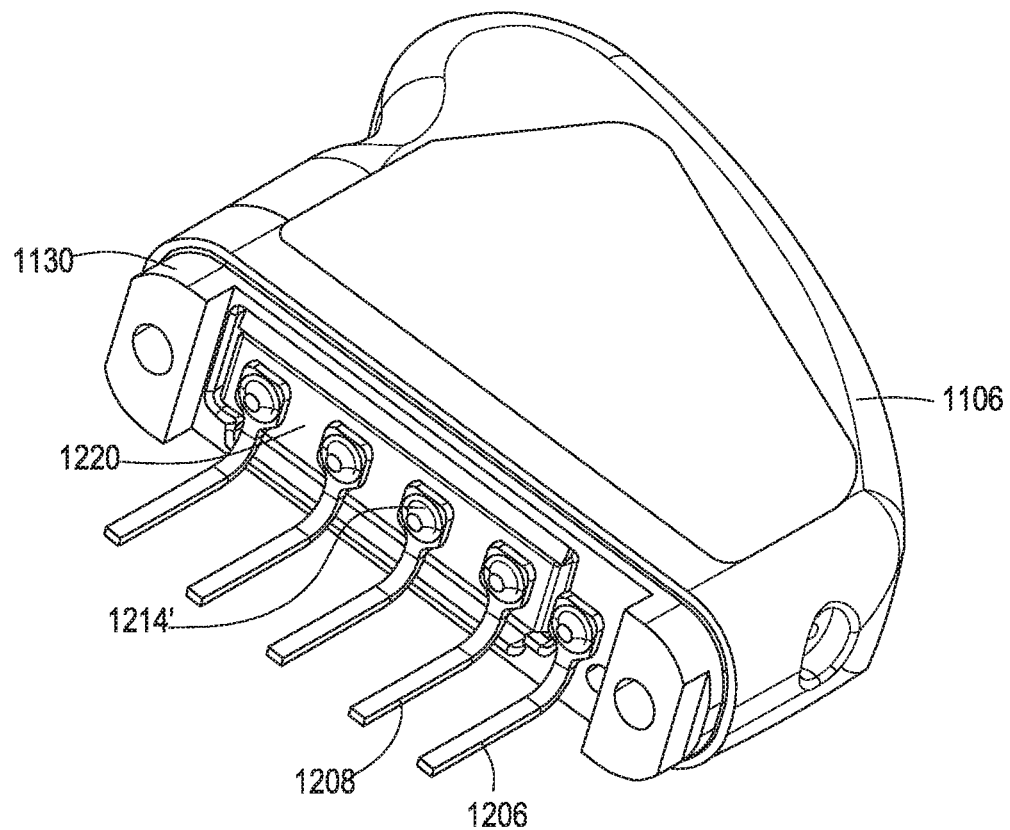
FIG. 29 shows a completed connector enclosure assembly.

A completed connector enclosure assembly 1106 is shown in FIG. 29. Here, the annular rings of the conductors 1206, 1208 have been bonded to the ground pin 1260 and feedthrough pins 1136, such as by reflowing solder 1214' as shown, and the common tab 1204 has been broken free and discarded. At this point, the conductors 1206, 1208 are ready to be bonded to pads of the hybrid.

Figure 30:
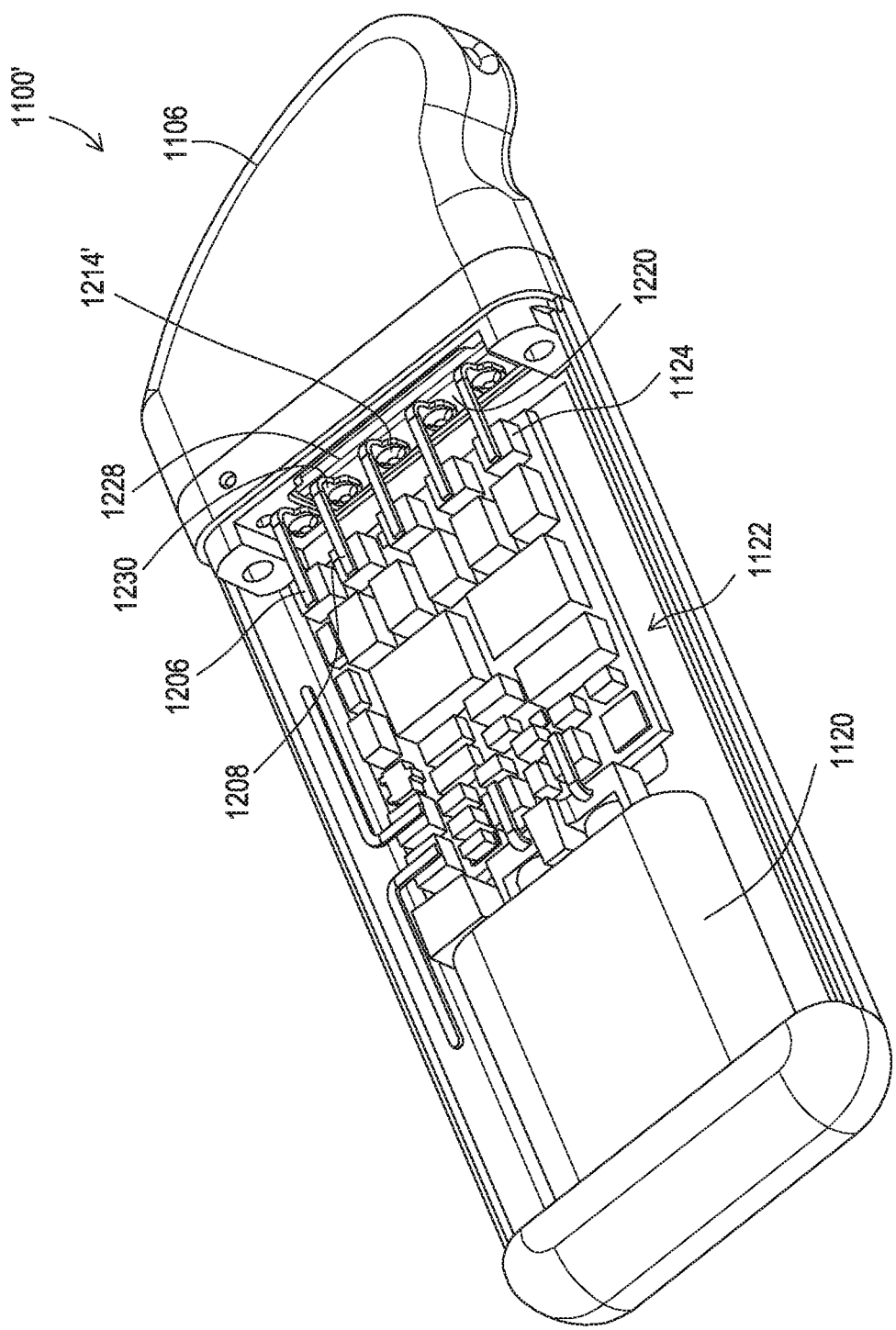
FIG. 30 shows the connector enclosure assembly upon being joined to hybrid circuitry during assembly of the medical device.

FIG. 30 shows the connector enclosure assembly 1106 upon being joined to the hybrid circuitry 1122 during assembly of the medical device 1100'. In this particular example, the baseplate 1130 has been bonded to one half of the can while the conductors 1206, 1208 have been soldered to pads 1124 of the hybrid to complete the physical and electrical coupling of the conductors 1206, 1208 to the hybrid. As discussed above for other embodiments, other manners of constructing the device 1100' are also possible, such as constructing the whole can separately, bonding the conductors 1206, 1208 to the pads 1124, and then inserting the hybrid circuitry 1122 into the assembled can while bonding the baseplate 1130 to the assembled can.

Figure 31:
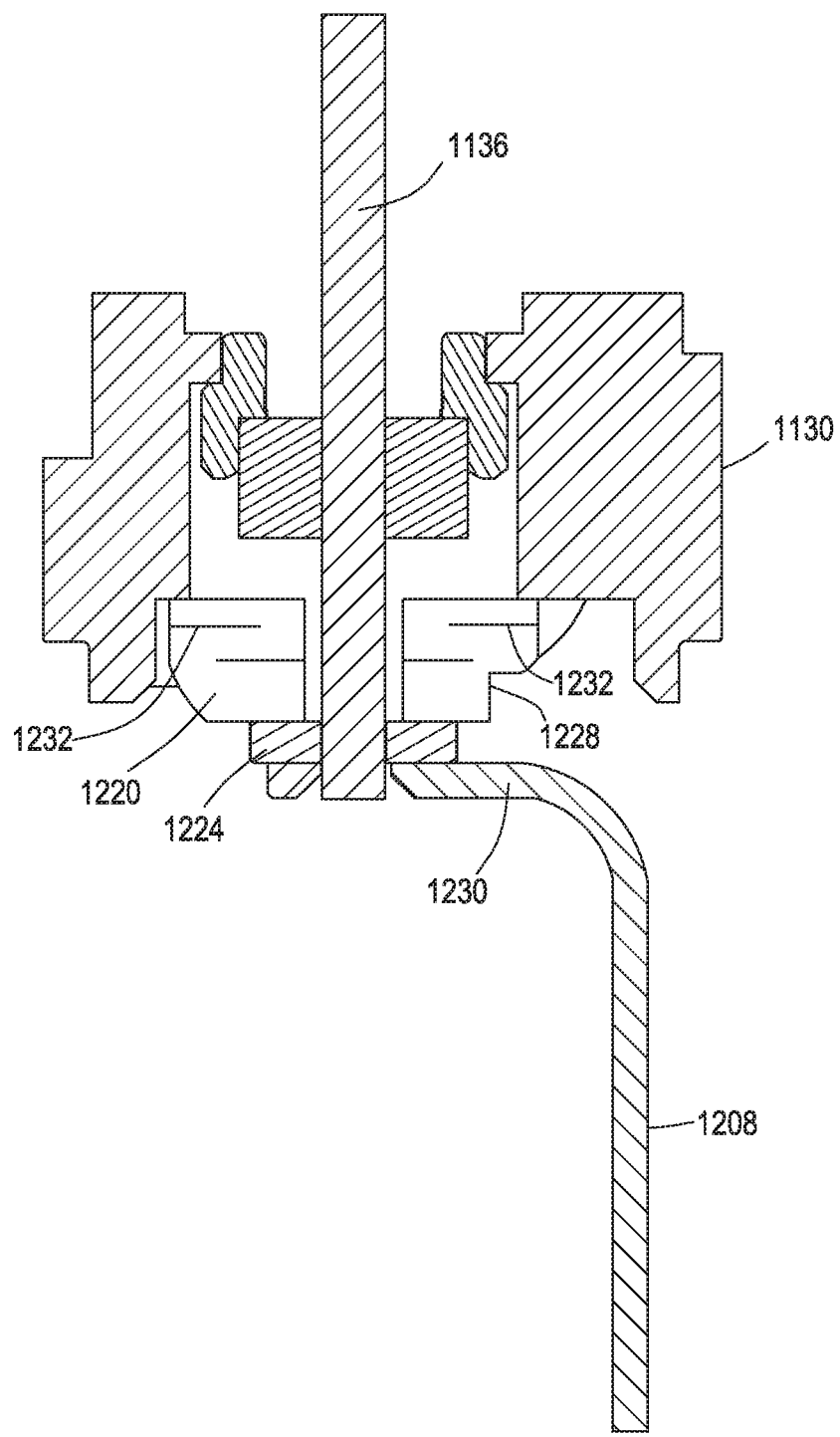
FIG. 31 shows an example where an annular ring has been welded to the pin with a protective washer in place.

Another aspect that is present in the embodiment shown in FIG. 30 as a recess 1228 within the filter capacitor 1220 in proximity to a transitional section 1230 of each conductor 1208, where the transactional section extends from the annular ring to where the conductor 1208 becomes approximately perpendicular to the plane of the filter capacitor 1220. As shown in FIG. 31, the ground plate 1232 of the filter capacitor 1220 is exposed at the outer edges so that soldering electrically couples the ground plate 1232 to the baseplate 1130. Furthermore, the ground plate 1232 may terminate to a metallic layer such as silver-palladium on the exterior side of the filter capacitor 1220 that further allows the filter capacitor 1220 to be soldered to the baseplate 1130.

To ensure that the transitional area 1230 of each conductor 1208 does not electrically short circuit to ground, the notch 1228 is present in the filter capacitor 1220 to create additional airspace between the exposed area of ground plate 1232 where the ground plate 1232 and any metallic layer on the outer surface is soldered and the transitional area 1230. While FIG. 31 shows an example where the annular ring has been welded to the pin 1136 with the protective washer 1224 in place, it will be appreciated that his configuration of the filter capacitor 1220 with the notch 1228 is also applicable to examples where the annular ring is soldered to the feedthrough pin 1136.

Figure 32:
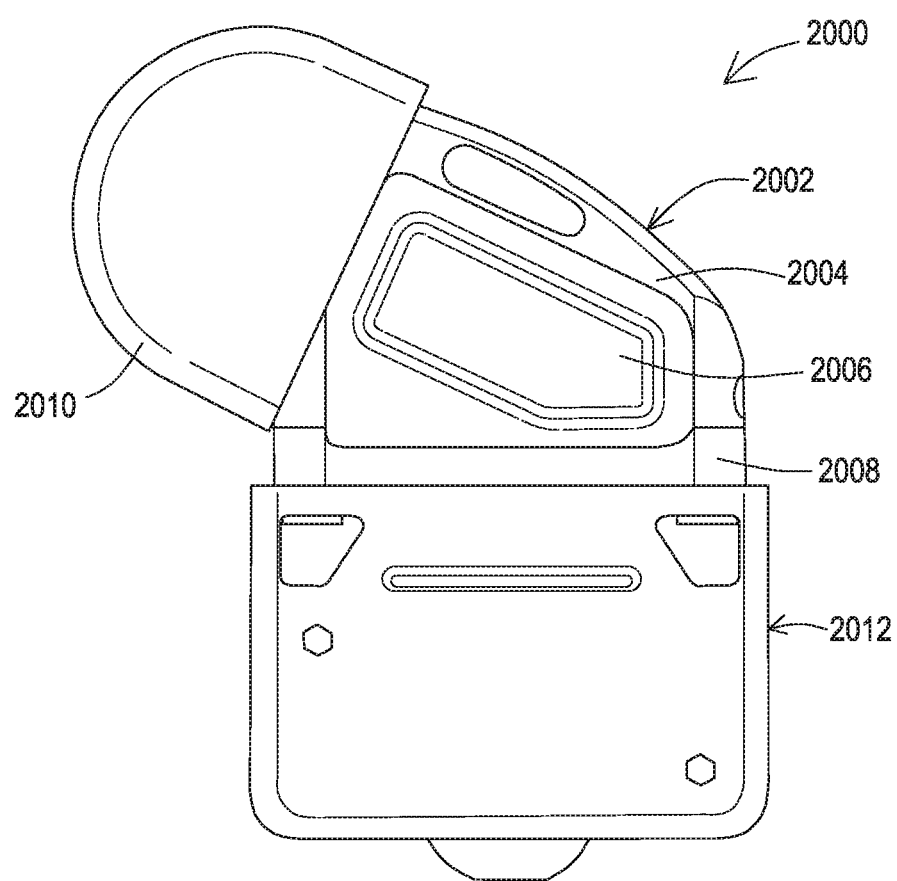
FIG. 32 shows an embodiment of a connector enclosure assembly with a protective cover for the feedthrough pins and a connector enclosure cover for the connector enclosure assembly.

FIG. 32 shows a shipping and storage configuration 2000 for another embodiment of a connector enclosure assembly 2002. This embodiment of the connector enclosure assembly includes a housing 2004, and panel 2006, and a base 2008. In this example, each of these is machined, milled, or otherwise constructed from metal and then ultimately welded together. However, it will be appreciated that embodiments of the connector enclosure assembly 2002 could be manufacture in other ways using other materials, such as by molding of polymers.

In this example, the connector enclosure assembly 2002 has yet to be joined to the remainder of the medical device and therefore a protective cover 2012 is in place to protect the feedthrough connections. This protective cover 2012 may be the same as the protective cover 1174 in FIG. 24. In addition to the protective cover 2012, this configuration 2000 also includes another protective cover 2010. The protective cover 2010 acts as a bore plug, to plug both a lead passageway and a set screw passageway of the connector enclosure assembly 2002. By plugging the set screw passageway, a set screw may already be present within the set screw passageway and the bore plug of the protective cover 2010 prevents the set screw from exiting the set screw passageway during storage, transport, and handling. The protective cover 2010 may remain in position during installation of the connector enclosure assembly 2002 to the remainder of the medical device and during storage, transport, and handling thereafter. The clinician may then remove the protective cover 2010 at the time of installation of the medical device to the patient.

Figure 33:
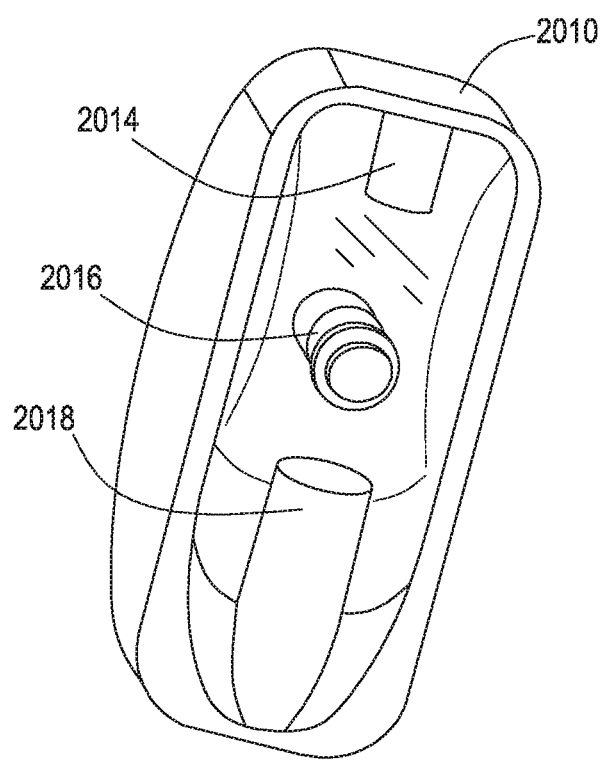
FIG. 33 shows the connector enclosure cover.

As shown in FIG. 33, the interior of this example of a protective cover 2010 includes a first bore plug 2016 and a second bore plug 2014. The first bore plug 2016 is inserted into the lead passageway of the connector enclosure assembly 2002 while the second bore plug 2014 is inserted into the set screw passageway of the connector enclosure assembly 2002. These bore plugs 2014, 2016 may establish an interference fit with the respective passageways. The first bore plug 2016 extends into the lead passageway and intersects the set screw passageway so that the set screw cannot enter the lead passageway while the protective cover 2010 is installed. This ensures that the set screw does not block the lead passageway when a clinician is attempting to insert the medical lead after removing the protective cover 2010. The second bore plug 2014 extends from the external surface of the housing 2004 to the set screw to prevent the set screw from moving out of the set screw passageway.

In this example, the protective cover 2010 also includes a bottom vertical post 2018 which abuts an underside of a protruding portion of the connector enclosure assembly 2002 to further support and affix the protective cover 2010 in place. For embodiments of the housing 2004 where a set screw passageway extends through the protruding portion 2020, as shown below in FIG. 37, the bottom vertical post may enter the bottom side of the set screw passageway to further aid in holding the protective cover 2010 in place. In embodiments such as that shown below in FIG. 36, the protective cover 2010 may alternatively omit the bottom post such that the interior of the protective cover 2010 rests against the protruding portion 2020.

The protective cover 2010 may be constructed of various materials such as liquid silicone rubber (LSR) or other materials with similar mechanical properties. The material of the protective cover 2010 allows for the protective cover 2010 to be adequately compliant for insertion into and removal from both passageways while establishing an interference fit.

Figure 34:
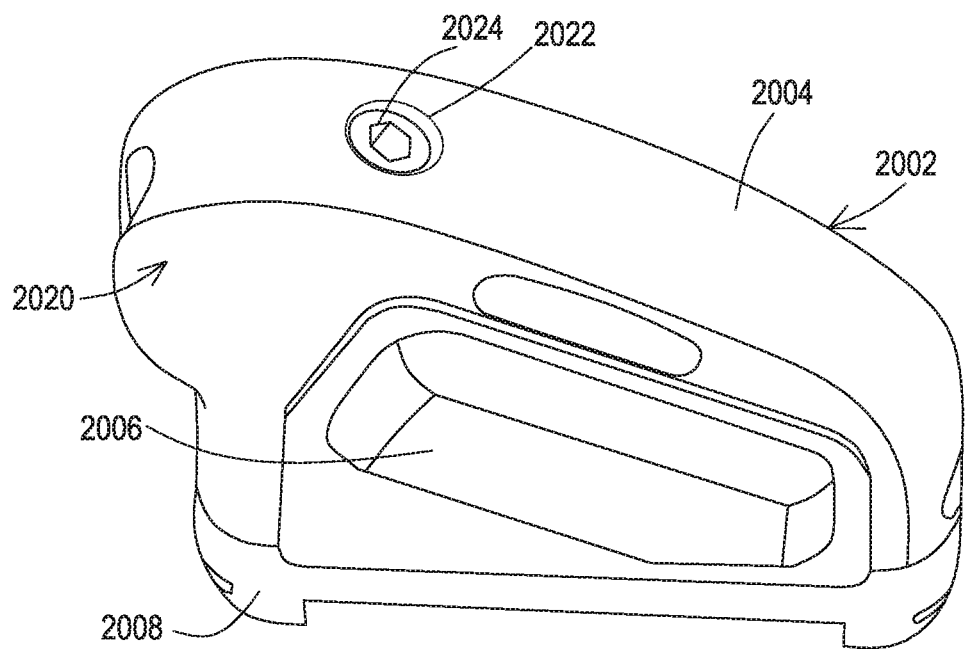
FIG. 34 shows another view of the connector enclosure assembly with a set screw in place.

FIG. 34 shows the connector enclosure assembly 2002 from a perspective where a protruding portion 2020 can be seen. A very similar protruding portion is also visible for the embodiments disclosed above such as in FIGS. 9, 10, 24, 29, and 30, which is further discussed below in relation to FIG. 37. Additionally, it can be seen in FIG. 34 that a set screw 2024 is present within an opening 2022 defining the set screw passageway. For embodiments where the housing 2004 is constructed of metal, this opening 2022 may be machined into the housing 2004 with threaded cylindrical walls such that the set screw 2024 is being threaded directly into the housing 2004. In other embodiments, a separate set screw block having the threaded cylindrical walls to receive the set screw 2024 may be installed within the housing 2004 rather than have the housing 2004 provided the threads.

Figure 35:
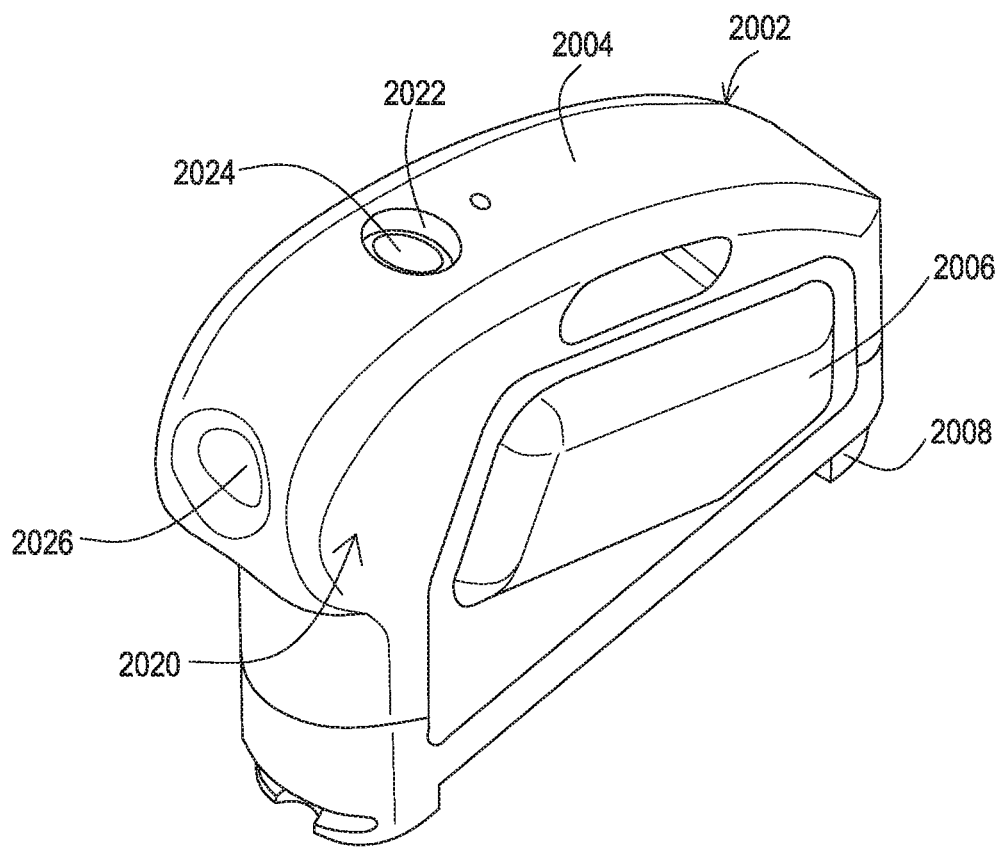
FIG. 35 shows another view of the connector enclosure assembly with the set screw in place in relation to the lead passageway opening.

FIG. 35 shows the connector assembly 2002 from a perspective where an opening 2026 establishing an entry way to the lead passageway is present on the protruding portion 2020 of the connector enclosure assembly 2002. The second bore plug 2014 of FIG. 33 enters the opening 2022 while the first bore plug 2016 enters the opening 2026.

Figure 36:
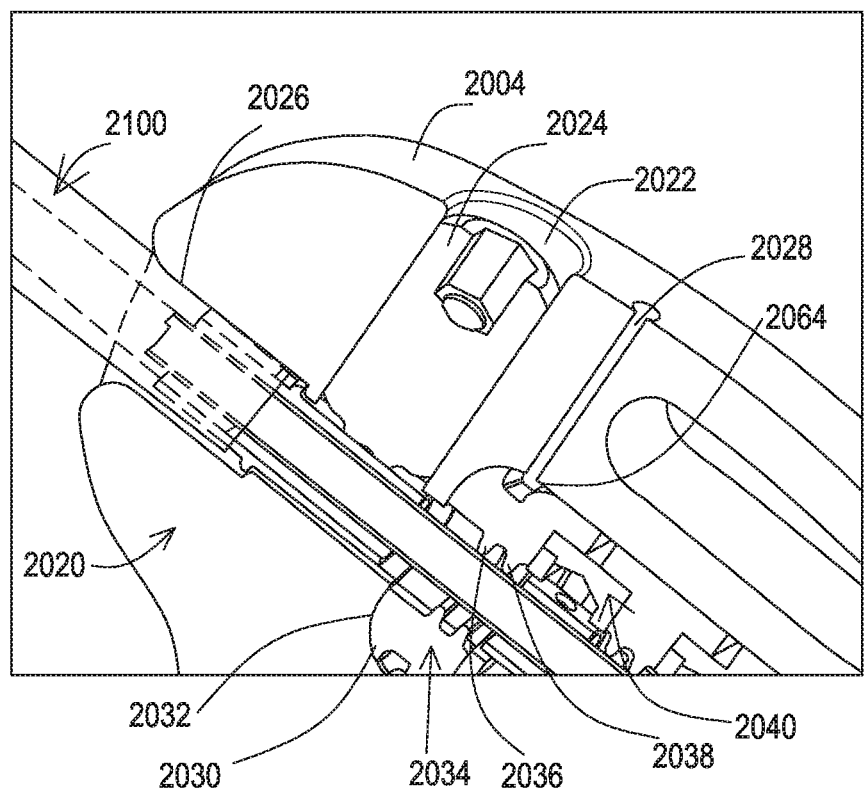
FIG. 36 shows a cross-sectional view of an embodiment of the connector enclosure assembly with a medical lead present within the lead passageway.

FIG. 36 shows a cross-sectional view of the connector assembly 2002 which reveals the intersecting nature of the set screw passageway defined by the opening 2022 and the lead passageway defined by the opening 2026. As can be seen here, the set screw 2024 and set screw passageway are at least partially present within the protruding portion 2020. The set screw 2024 may be tightened against the medical lead 2100 to secure the medical lead 2100 in position within the lead passageway. FIG. 36 further shows that in this embodiment the set screw 2024 is threaded directly into the opening 2022 formed by the housing 2004.

In the embodiment of FIG. 36, the set screw 2024 acts as a dummy electrical connector in a most distal position, as there is no electrical conductor connecting the set screw 2024 back to the hybrid of the medical device. As a result, the set screw 2024 may be exposed to the tissue of the patient such that a grommet is not needed to cover the set screw 2024. The set screw 2024 being in electrical connection with the housing 2004 in this example allows the set screw 2024 to establish an electrical connection from a connector on the lead body 2100 to the housing 2004 and/or tissue. Such a connection to the housing 2004 allows the screw 2024 to electrically ground a electromagnetic shield that may be present within the lead body 2100 for purposes of magnetic resonance imaging (MRI) safety.

The housing 2004 also defines an elongated chamber 2064 that houses electrical connectors 2040 surrounded by seals such as a distal most seal 2034 and aligns the electrical connectors 2040 with the opening 2026 to further define the lead passageway. In this particular example, the seals including the distal most seal 2034 include two axially spaced circumferential sealing ridges 2036 and 2038 to ensure that the electrical connectors are adequately sealed from body fluids that may migrate into the lead passageway. Having two circumferential sealing ridges 2036, 2038 aids in sealing the lead where there may be some degree of misalignment of the connectors of the lead body and the connectors of the connector enclosure assembly 2002.

In this example, the elongated chamber 2064 of the housing 2004 includes a distal abutment 2032 that separates the area where the set screw 2024 is located relative to the area where the electrical connectors 2040 are present. One or more of the electrical connectors 2040 are actively driven by the hybrid circuitry of the medical device and therefore adequate electrical separation ensures that the housing 2004 and set screw 2024 are not inadvertently made active.

The most distal seal 2034 of this example includes a flap 2030 on the distal side which rests against the abutment 2032. The elongated chamber 2064 of the housing 2004 may be filled with a non-conductive filler material such as LSR, and this filler material engages the flap 2030 to force the flap to seal against the abutment 2032. The housing 2004 also includes a filler vent 2028 that allows the excess filler material to escape from the elongated chamber 2064 within the housing 2004. The filler vent 2028 may have a consistent diameter as shown, or may have a varying diameter such as, for example, a counterbore at the outer surface of the housing 2004.

FIG. 36 also illustrates that the electrical connectors 2040, such as Bal Seal® connectors, are flangeless. This allows the intervening seals 2034 to omit grooves for accepting flanges that ultimately reduces the width of the seals 2034 and connector to connector spacing while the seals 2034 surround an outer circumferential surface of the electrical connectors 2040.

Figure 37:
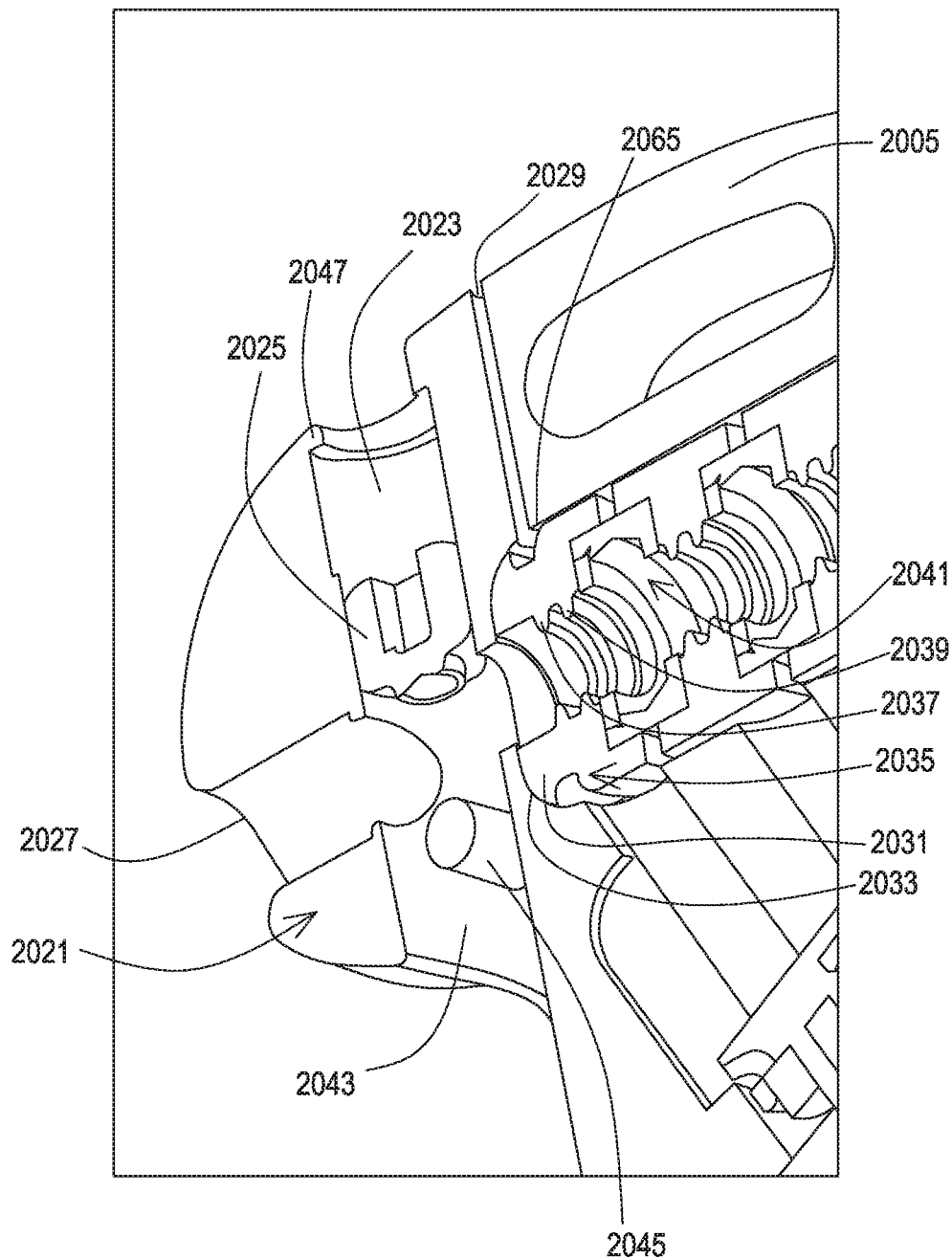
FIG. 37 shows a cross-sectional view of another embodiment of the connector enclosure assembly.

FIG. 37 shows an example of a housing 2005 that utilizes additional features to retain a set screw 2025. The housing 2005 includes an opening 2023 with threaded cylindrical walls to define the set screw passageway which the set screw 2025 engages. However, a flange 2047 is present to retain the set screw 2025. Because the flange 2047 defines an opening that is smaller than the diameter of the set screw 2025, the set screw 2025 is installed from the opposite end of the set screw passageway through an opening 2043. The opening 2043 further defines the set screw passageway that extends completely through the protruding portion 2021. In this example, a pin 2045 is subsequently placed through the portion of the set screw passageway to block the set screw 2025 from escaping through the opening 2043 and to further support the medical lead when the set screw is tightened. This set screw and pin relationship is also shown above in FIG. 11.

The remaining features of the connector enclosure assembly of FIG. 37 are similar to that of FIG. 36. The lead passageway is defined by an opening 2027 present within the protruding portion 2021. The elongated chamber 2065 defines an abutment 2033 upon which a flap 2031 of a most distal seal 2035 rests. The seal 2035 includes one or more sealing ridges 2037, 2039. A filler vent 2029 is present to allow the excess filler to escape upon forcing the flap 2031 against the abutment 2033. Additionally, the series of electrical connectors 2041 separated by intervening seals are present within the elongated chamber 2065 of the housing 2005.

Figure 38:
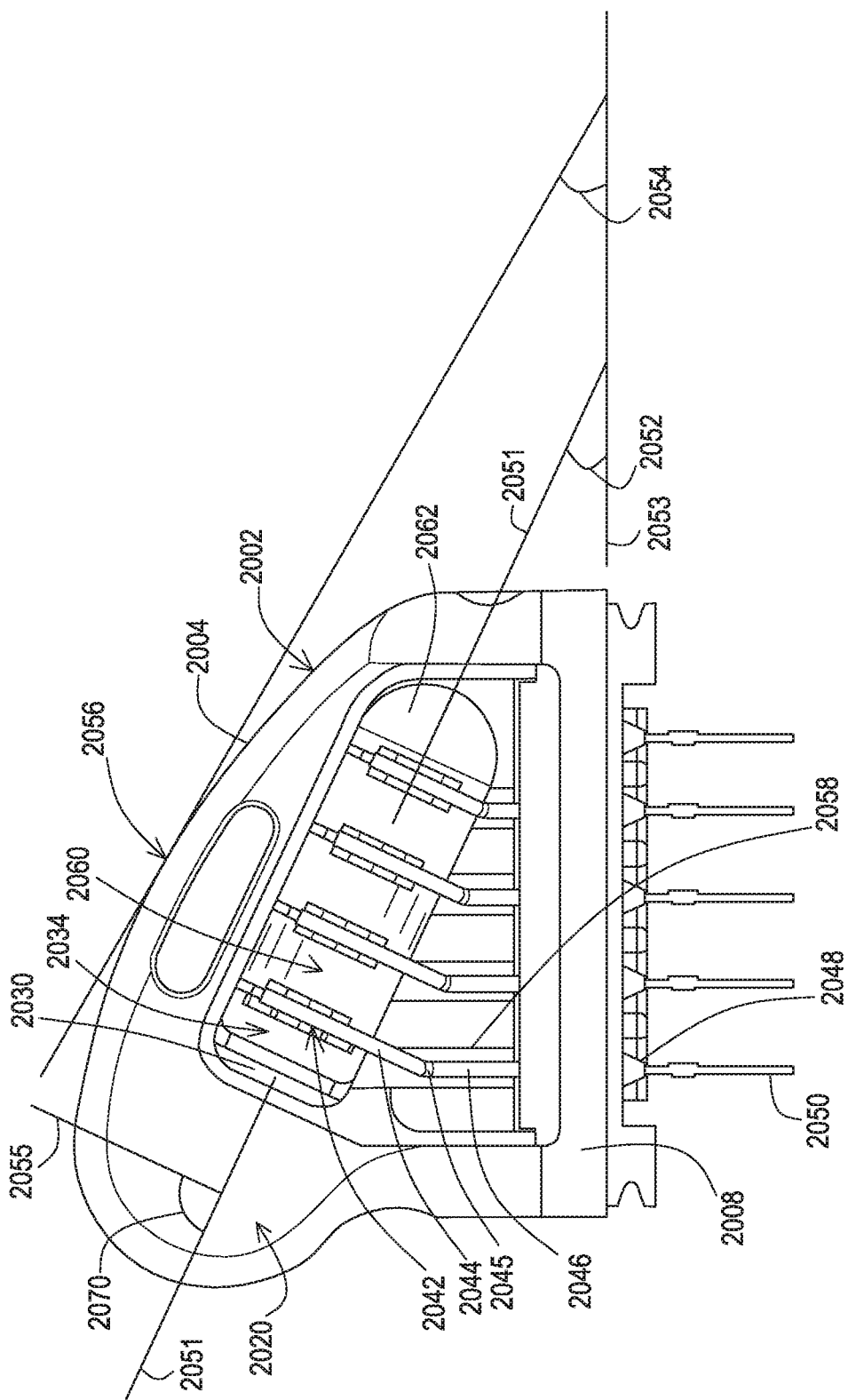
FIG. 38 shows a view of the connector enclosure assembly with a side panel removed to reveal seals, electrical connectors, and feedthrough pins within the housing.

FIG. 38 shows the connector enclosure assembly 2002 with the panel 2006 removed to reveal the relationship of the seals 2034, 2060, 2062; the exposed electrical connector area 2042; and feedthrough pin sections 2044, 2045, and 2046. FIG. 38 also illustrates the angled nature of the lead passageway and the housing 2004. In this example, the series of electrical connectors 2040 positioned adjacently with intervening seals 2060 complete the lead passageway from the opening 2026. The lead passageway has an axial dimension 2051 that creates an angle 2052 with respect to a plane 2053 defined by the base 2008. The plane 2053 may be established by a surface feature of the base 2008 such as a lip, flange, or other surface that establishes contact with a can of the medical device upon mounting of the connector assembly 2002 to the medical device. This angle 2052 is greater than zero degrees and less than 90 degrees. For example, this angle 2052 may be 10 degrees or greater in one embodiment, 25 degrees or greater in another embodiment, 45 degrees or greater in another embodiment, and 60 degrees or greater in yet another embodiment.

In this embodiment, the axial dimension 2051 is also in a different plane than the axial dimension 2055 of the set screw passageway so as to form an angle 2070. In the particular example shown in FIG. 38, the axial dimension 2051 is at an angle 2070 of 90 degrees from the axial dimension 2055.

In this embodiment, the housing 2004 itself has an angled configuration. This angled configuration is evident by a mid-point tangent 2056 being at an angle 2054 relative to the plane 2053 of the base 2008. To achieve this angled configuration, the angle 2054 is greater than zero degrees and less than 90 degrees. In some embodiments this angle 2054 may be the same as the angle 2052, while in other embodiments, the two angles 2052 and 2054 may be different.

In this embodiment, it can further be seen that the housing 2004 and the protruding portion 2020 form separate arcs. The radius of curvature of the arcs are different, with the radius of curvature of the arc formed by the protruding portion 2020 being smaller in this example. For instance, the radius of curvature of the arc of the surface of the housing 2004, which extends from the protruding portion 2020 in this particular example, may be measured at the mid-point defining the tangent 2056 while the arc of the protruding portion 2020 may be measured at the intersection with the axial dimension 2051.

To facilitate the connection of the feedthrough pins to the electrical connectors, the feedthrough pins of this example are provided with multiple sections 2044, 2045, and 2046. These multiple sections are also visible in FIG. 11. One section 2046 extends upward from the feedthrough connection 2048 with the hybrid conductor 2050 and is perpendicular to the plane 2053. The housing 2004 defines a channel 2058 that accommodates the section 2046. Another section 2044 is angled relative to the section 2046 so as to be approximately perpendicular to the axial dimension 2051 of the lead passageway. By being angled in relation to the section 2046, the section 2044 properly aligns with and contacts the exposed electrical connector area 2042 so as to make proper electrical connection with the electrical connector defining the lead passageway.

In this particular example, the feedthrough pin section 2046 is positioned by the feedthrough connection 2048 where the feedthrough pin section 246 has exited the housing 2004. This positioning of the pin section 2046 defines a longitudinal dimension of the pin 246 that intersects with the lead passageway other than at the exposed area 2042. An intervening section 2045 interconnects the section 2046 and the section 2044 and is angled with respect to both the section 2046 and the section 2044 so as to offset the section 2044 from the section 2046. As illustrated in FIG. 38, section 2045 is essentially pointing out of the page to provide this offset which brings the section 2044 into contact with the exposed area 2042. It will be appreciated that linear feedthrough pins may also be appropriate such as when the feedthrough connection of the feedthrough pins aligns the feedthrough pins to the electrical connectors.

Figure 39:
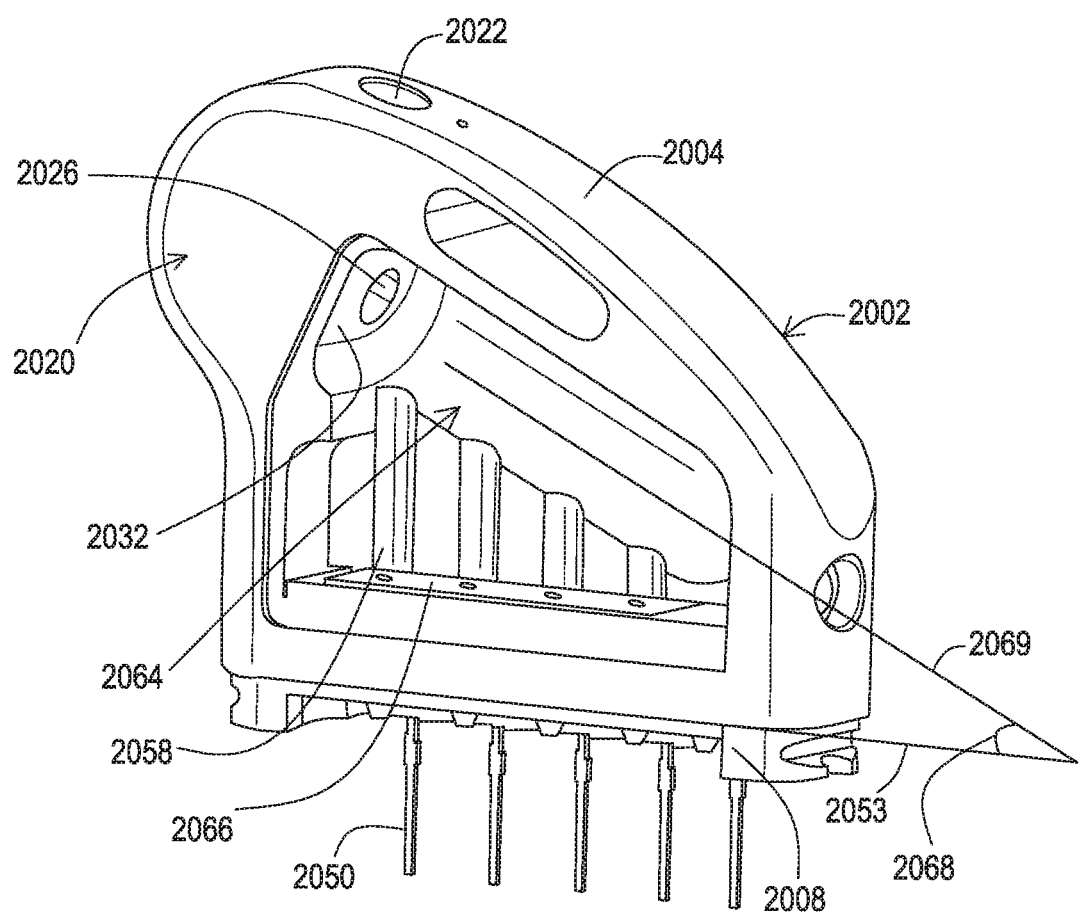
FIG. 39 shows a view of the connector enclosure assembly with a side panel, seals, electrical connectors, and feedthrough pins removed to reveal within the housing.

FIG. 39 shows the housing 2004 with the seals, electrical connectors, and feedthrough pin sections removed. Here, the elongated chamber 2064 defined by the housing 2004 can be seen. It will be appreciated that the indented panel 2006 as shown in FIG. 35 that is omitted from this figure may also further define the elongated chamber 2064. The elongated chamber 2064 can be seen as having an axial dimension 2069 that forms an angle 2068 with the plane 2053 of the base 2008. In this example, the angle 2068 is the same value as the angle 2052 of FIG. 38, considering the elongated chamber 2064 establishes the angle of the seals and electrical connectors forming the lead passageway.

FIG. 39 also shows the relationship of the feedthrough pin channels 2058 relative to a feedthrough 2066 integrated into the base 2008 of this example. In this example, the feedthrough pin channels 258 extend from the feedthrough 2066 up to the elongated chamber 2064.

Thus, in the examples shown and described above, the connector enclosure assembly provides an angled lead passageway in conjunction with various other features. The relative size of the connector enclosure assembly and/or the direction of the medical lead exiting the connector enclosure assembly within the pocket may be beneficial to implantation procedure as a result.

While embodiments have been particularly shown and described, it will be understood by those skilled in the art that various other changes in the form and details may be made therein without departing from the spirit and scope of the invention.

What is claimed is:

1. An implantable medical device, comprising:
    an enclosure that comprises a sleeve having an open top end and an open bottom end, wherein at least a portion of the sleeve has a geometry that is machined from biocompatible material comprising titanium, the enclosure further comprising a top cap attached to the sleeve and spanning the open top end and a bottom cap attached to the sleeve and spanning the open bottom end, with a seam formed at a connection between the bottom cap and the bottom end of the sleeve and with the bottom cap comprising at least one side that extends from the seam in a direction away from the sleeve;
    a battery within the enclosure;
    circuitry within the enclosure; and
    a connector block module assembly that comprises a connector block module body and at least one lead connection within the connector block module body, the connector block module body being fixed to the top cap of the enclosure, the connector block module body comprising an external surface, an opening on the external surface, and a channel from the opening through the connector block module body to the at least one lead connection.

2. The implantable medical device of claim 1, wherein at least one of the top cap and bottom cap is welded to the sleeve.

3. The implantable medical device of claim 1, wherein the biocompatible material is bar stock.

4. The implantable medical device of claim 1, wherein the biocompatible material is tubular stock.

5. The implantable medical device of claim 1, wherein the sleeve is formed of two halves that are electric discharge machined from material.

6. The implantable medical device of claim 5, wherein an inside geometry and an outside geometry of the two halves are wire electric discharge machined.

7. The implantable medical device of claim 5, wherein an inside geometry of the two halves is wire electric discharge machined and an outside geometry of the two halves is milled, and wherein the two halves are annealed.

8. The implantable medical device of claim 1, wherein an inside geometry and an outside geometry of the enclosure are wire electric discharge machined.

9. The implantable medical device of claim 1, wherein an inside geometry of the enclosure is wire electric discharge machined and an outside geometry of the enclosure is milled, and wherein the sleeve is annealed.

10. The implantable medical device of claim 9, wherein the material has a hardness of grade five titanium or harder.

11. The implantable medical device of claim 10, wherein the material is titanium of grade five or harder.

12. The implantable medical device of claim 1, wherein an inside geometry and an outside geometry of the enclosure is milled, and wherein the sleeve is annealed.

13. An implantable medical device, comprising:
    an enclosure that comprises a middle piece having an open top end and an open bottom end, wherein at least a portion of the middle piece has a geometry that is machined from biocompatible material comprising titanium, the enclosure further comprising a top cap attached to the middle piece and spanning the open top end and a bottom cap attached to the middle piece and spanning the open bottom end, with a seam formed at a connection between the bottom cap and the bottom end of the of the middle piece and with the bottom cap comprising at least one side that extends from the seam in a direction away from the middle piece;
    a battery within the enclosure;
    circuitry within the enclosure; and
    a connector block module assembly that comprises a connector block module body and at least one lead connection within the connector block module body, the connector block module body being fixed to a top of the enclosure, the connector block module body comprising an external surface, an opening on the external surface, and a channel from the opening through the connector block module body to the at least one lead connection.

14. The implantable medical device of claim 13, wherein at least one of the top cap and bottom cap is welded to the middle piece.

15. The implantable medical device of claim 13, wherein the biocompatible material is bar stock.

16. The implantable medical device of claim 13, wherein the biocompatible material is tubular stock.

17. The implantable medical device of claim 13, wherein the middle piece is formed of two halves that are electric discharge machined from material.

18. The implantable medical device of claim 13, wherein the material is titanium of grade five or harder.

19. The implantable medical device of claim 13, wherein the middle piece is annealed.

20. An implantable medical device, comprising:
an enclosure that comprises a sleeve having an open top end and an open bottom end, wherein at least a portion of the sleeve has a geometry that is machined from biocompatible material that comprises titanium, the enclosure further comprising a top cap attached to the sleeve by a weld and spanning the open top end and a bottom cap attached to the sleeve and spanning the open bottom end, the top cap comprising a metal, with a seam formed at a connection between the bottom cap and the bottom end of the sleeve and with the bottom cap comprising multiple sides that extend from the seam in a direction away from the sleeve;
a battery within the enclosure;
circuitry within the enclosure; and
a connector block module assembly that comprises a connector block module body and at least one lead connection within the connector block module body, the connector block module body comprising a polymer and being fixed directly to the top cap of the enclosure, the connector block module body comprising an external surface, an opening on the external surface, and a channel from the opening through the connector block module body to the at least one lead connection.

* * * * *